US006025325A

United States Patent [19]
Campfield et al.

[11] Patent Number: 6,025,325
[45] Date of Patent: *Feb. 15, 2000

[54] PEGYLATED OBESE (OB) PROTEIN COMPOSITIONS

[75] Inventors: Arthur Campfield, Verona, N.J.; Rene Devos, Kaaistraat; Yves Guisez, Zandstraat, both of Belgium

[73] Assignee: Hoffman-La Roche Inc., Nutley, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/648,263

[22] Filed: May 15, 1996

Related U.S. Application Data

[63] Continuation-in-part of application No. 08/484,629, Jun. 7, 1995, which is a continuation-in-part of application No. 08/435,777, May 5, 1995.

[51] Int. Cl.$^7$ .......................... A61K 38/22; A61K 38/00
[52] U.S. Cl. .................... 514/2; 514/8; 514/12; 514/909; 530/399; 530/350; 530/351; 530/402; 530/403; 530/404; 530/405; 530/406; 424/85.1; 424/193.1; 424/185.1; 424/194.1; 424/195.11; 424/198.1
[58] Field of Search .................... 530/350, 351, 530/399, 402–406; 514/2, 81.2; 474/85.2, 185.1, 193.1, 194.1, 195.11, 198.1

[56] References Cited

U.S. PATENT DOCUMENTS

| | | | |
|---|---|---|---|
| 4,199,337 | 4/1980 | Davis et al. | 435/181 |
| 4,609,546 | 9/1986 | Hiratoni et al. | 424/85.2 |
| 4,643,969 | 2/1987 | Inouye et al. | . |
| 4,666,836 | 5/1987 | Inouye et al. | . |
| 4,757,013 | 7/1988 | Inouye et al. | . |
| 5,559,208 | 9/1996 | Basinski et al. | . |
| 5,563,243 | 10/1996 | DiMarchi et al. | . |
| 5,563,244 | 10/1996 | DiMarchi et al. | . |
| 5,563,245 | 10/1996 | DiMarchi et al. | . |
| 5,567,678 | 10/1996 | DiMarchi et al. | . |
| 5,567,803 | 10/1996 | Basinski et al. | . |
| 5,569,743 | 10/1996 | DiMarchi et al. | . |
| 5,569,744 | 10/1996 | Basinski et al. | . |
| 5,574,133 | 11/1996 | DiMarchi et al. | . |
| 5,580,954 | 12/1996 | DiMarchi et al. | . |
| 5,594,104 | 1/1997 | Basinski et al. | . |

FOREIGN PATENT DOCUMENTS

| | | |
|---|---|---|
| 0154316 | 9/1985 | European Pat. Off. . |
| 0 510 356 | 10/1992 | European Pat. Off. . |
| 0510356 | 10/1992 | European Pat. Off. . |
| 0 725 078 | 8/1996 | European Pat. Off. . |
| 0 725 079 | 8/1996 | European Pat. Off. . |
| 2 292 382 | 2/1996 | United Kingdom . |
| 9511924 | 5/1995 | WIPO . |
| WO 95/11924 | 5/1995 | WIPO . |
| WO 96/05309 | 2/1996 | WIPO . |
| WO 96/21469 | 7/1996 | WIPO . |
| WO 96/22308 | 7/1996 | WIPO . |
| WO 96/31526 | 10/1996 | WIPO . |
| WO 96/40912 | 12/1996 | WIPO . |
| WO 97/20933 | 6/1997 | WIPO . |
| WO 97/24440 | 7/1997 | WIPO . |

OTHER PUBLICATIONS

Gen Bank Accession No. 18812.
Gen Bank Accession No. 18915.
Gen Bank Accession No. 03288.
Gen Bank Accession No. 23332.
Yamasaki, et al., Novel Polyethylene Glycol Derivatives for Modification of Proteins, Agric. Biol. Chem. vol. 52, No. 8, pp. 2125–2127 (1988).
Yamasaki, et al., Some Properties of Ricin D Modified with a Methoxypolyethylene Glycol Derivative, Agric. Biol. Chem, vol. 54, No. 10, pp. 2635–2640 (1990).
Zhang, et al, Positional Cloning of the mouse obese gene and its human homologue, Nature, vol. 372, pp. 425–432 (1994).
DeSutter, et al, Production of enzymatically active rat protein disulfide isomerase in *Escherichia coli,* Gene, vol. 141, pp. 163–170 (1994).
Friedman, J. M. et al., *Genomics* 11:1054–62 (1991).
Murakami, et al, Cloning of Rat Obese cDNA and its Expression in Obese Rats, Biochemical and Biophysical Research Communications, vol. 209, No. 3, pp. 944–952, (1995).
Masuzaki, et al., Adipocyte–Specific Expression and Regional Differences in the Adipose Tissue, Diabetes, vol. 44, pp. 855–858 (1995).
Lindpaintner, Finding An Obesity Gene—A Tale of Mice and Man, Clinical Implications of Basic Research, vol. 332, No. 10, pp. 679–680 (1995).
Geffroy, et al., Localization of the Human OB Gene (OBS) to Chromosome 7q32 by Fluorescence in Situ Hybridization, Genomics, vol. 28, pp. 603–604 (1995).
Masuzaki, et al., Adipose Tissue–Specific Expression of the Obese (ob) Gene in Rats and its Marked Augmentation in Genetically Obese–hyperglycemic Wistar Fatty Rats, Proc. Japan Acad, vol. 71, pp. 148–152 (1995).
Green, et al., The Human Obese (OB) Gene:RNA Expression Pattern and Mapping on the Physical, Cytogenetic, and Genetic Maps of Chromosome 7, Genome Research, vol. 5, pp. 5–12 (1995).
Altmann, et al., Expression and Purification of a Synthetic Human Obese Gene Product, Protein Expression and Purification, vol. 6, pp. 722–726 (1995).
Hamilton, et al., Increased obese mRNA expression in omental fat cells from massively obese humans, Nature Medicine, vol. 1, No. 9, pp. 953–956 (1995).

(List continued on next page.)

*Primary Examiner*—Garnette D. Draper
*Attorney, Agent, or Firm*—George W. Johnston; William H. Epstein; Lewis J. Kreisler

[57] ABSTRACT

Polyethylene and polypropylene protein conjugates which modulate body weight of animals and humans for the treatment, prevention and control of obesity and associated diseases or conditions, and the recombinant expression of these biologically active proteins in purified and homogeneous forms.

2 Claims, 3 Drawing Sheets

OTHER PUBLICATIONS

Vydelingum, et al., Overexpression of the Obese Gene in the Genetically Obese JCR:LaA–Corpulent Rat, Biochemical and Biophysical Research Communications, vol. 216, No. 1, pp. 148–153 (1995).

Barinaga, Obese Protein Slims Mice, Science, vol. 269, pp. 475–476 (1995).

Considine, et al., Evidence Against Either a Premature Stop Codon or the Absence of Obese Gene mRNA in Human Obesity, J. Clin. Invest., vol. 95, pp. 2986–2988 (1995).

Funahashi, et al., Enhanced Expression of Rat Obese (ob) Gene in Adipose Tissues of Ventromedial Hypothalamus (VMH)–Lesioned Rats, Biochemical and Biophysical Research Communications, vol. 211, No. 2, pp. 469–475 (1995).

Olefsky, Weighing in on the Lean Genes, J. Clin. Invest., vol. 95, pp. 2427–2428 (1995).

De Vos, Induction of ob Gene Expression by Corticosteroids Is Accompanied by Body Weight Loss and Reduced Food Intake, The Journal of Biological Chemistry, vol. 270, No. 27, pp. 15958–15961 (1995).

Halaas, et al., Weight–Reducing Effects of the Plasma Protein Encoded by the obese Gene, Science, vol. 269, pp. 543–546 (1995).

Pelleymounter, et al., Effects of the obese Gene Product on Body Weight Regulation in ob/ob Mice, Science, vol. 269, pp. 540–543 (1995).

Stirling, et al., Identification of Microsatellite Markers Near the Human ob Gene and Linkage Studies in NIDDM–Affected Sib Pairs, Diabetes, vol. 44, pp. 999–1001 (1995).

Frederich, et al., Expression of ob mRNA and its Encoded Protein in Rodents, J. Clin. Invest., vol. 96, pp. 1658–1663 (1995).

MacDougald, et al., Regulated expression of the obese gene product (leptin) in white adipose tissue and 3T3–L1 andipocytes, Proc. Natl. Acad. Sci, vol. 92, pp. 9034–9037 (1995).

Ogawa, et al., Molecular Cloning of Rat Obese cDNA and Augmented Gene Expression in Genetically Obese Zucker Fatty (fa/fa) Rats, J. Clin. Invest, vol. 96, pp. 1647–1652 (1995).

Rentsch, et al., Recombinant OB–Gene Produce Reduces Food Intake in Fasted Mice, Biochemical and Biophysical Research Communications, vol. 214, No. 1, pp. 131–136 (1995).

Trayhurn, et al. Effects of fasting and refeeding on ob gene expression in white adipose tissue of lean and obese (ob/ob) mice, FEBS Letters, vol. 368, pp. 488–490 (1995).

Madej, et al., Threading analysis suggest that the obese gene product may be a helical cytokine, FEBS Letters, vol. 373, pp. 13–18 (1995).

Maffei, et al., Leptin levels in human and rodent: Measurement of plasma leptin and ob RNA in obese and weight–reduced subjects, Nature Medicine, vol. 1, No. 11, pp. 1155–1161, (1995).

Cusin, et al., A Relationship Leading to Clues to the Understanding of Obesity, Diabetes, vol. 44, pp. 1467–1470 (1995).

Frederich, et al., Leptin levels reflect body lipid content in mice: Evidence for diet–induced resistance to leptin action, Nature Medicine, vol. 1, No. 12, pp. 1311–1314 (1995).

He, et al., Genomic Organization, Promoter Activity, and Activation by CCAAT/Enhancer–Binding Protein $\alpha$, The Journal of Biological Chemistry, vol. 270, No. 48, pp. 28887–28891 (1995).

Maffei, et al., Increased expression in adipocytes of ob RNA in mice with lesions of the hypothalamus and with mutations at the db locus, Proc. Natl. Acad. Sci., vol. 92, pp. 6957–6960 (1995).

Moinat, et al., Modulation of obese gene expression in rat brown and white adipose tissues, FEBS Letters, vol. 373, pp. 131–134 (1995).

Murakami, et al., Dexamethasone Regulates Obese Expression in Isolated Rat Adipocytes, vol. 214, No. 3, pp. 1260–1267 (1995).

Isse, Structural Organization and Chromosomal Assignment of the Human Obese Gene, The Journal of Biological Chemistry, vol. 270, No. 46, pp. 27728–27733 (1995).

Weigle, et al., Recombinant ob Protein Reduces Feeding and Body Weight in the ob/ob Mouse, J. Clin. Invest., vol. 96, pp. 2065–2070 (1995).

De Sutter, et al., Production of enzymatically active rat protein disulfide isomerase in *Escherichia coli*, Gene, vol. 141, pp. 163–170 (1994).

Takahara, et al., The ompA Signal Peptide Directed Secretion of Staphylococcal Nuclease A by *Escherichia coli*, The Journal of Biological Chemistry, vol. 260, No. 5, pp. 2670–2674 (1985).

Groch, et al., Synthesis of the *Bacillus subtilis* histone–like DNA–binding protein Hbsu in *Escherichia coli* and secretion into the periplasm,. Gene, vol. 124, pp. 99–103 (1993).

Barone, et al., The Expression in *Escherichia coli* of Recombinant Human Platelet Factor 4, a Protein with Immunoregulatory Activity, The Journal of Biological Chemistry, vol. 263, No. 18, pp. 8710–8715 (1988).

Hussain, et al., Expression of ricin B chain in *Escherichia coli*, FEBS Letters, vol. 244, No. 2, pp. 383–387 (1989).

Libby, et al., Expression and Purification of Native Human Granulocyte–Macrophage Colony–Stimulating Factor from an *Escherichia coli* Secretion Vector, DNA, vol. 6, No. 3, pp. 221–229 (1987).

Monteilhet, et al., Cytoplasmic and periplasmic production of human apolipoprotein E in *Escherichia coli* using natural and bacterial signal peptides, Gene, vol. 125, pp. 223–228 (1993).

Parker, et al., Overexpression of native human $\beta_2$–microglobulin in *Escherrichia coli* and its purification, Gene, vol. 83, pp. 117–124 (1989).

Le, et al., Purification of Secreted Recombinant Proteins from *Escherichia coli*, Purification and Analysis of Recombinant Proteins, Seetharam, et al., eds., Ch. 7, pp. 163–181 (in Dekker 1991).

Ghrayeb, et al., Secretion cloning vectors in *Escherichia coli*, The Embo Journal, vol. 3, No. 10, pp. 2437–2442 (1984).

Barthelemy, et al., Production and secretion of human interleukin 6 into the periplasm of *Escherichia coli*: efficient processing of N–terminal variants of hIL6 by the *E. coli* signal peptidase, Journal of Biotechnology, vol. 27, pp. 307–316 (1993).

Fischer, et al., Physiological consequence of expression of soluble and active hen egg white lysozyme in *Escherichia coli*, Applied Microbiol Biotechnol, vol. 39, pp. 537–540 (1993).

Cheah, et al., Secretion of eukaryotic growth hormones in *Escherichia coli* is influenced by the sequence of the mature proteins, Gene, vol. 138, pp. 9–15 (1994).

Becker, et al., Expression, secretion and folding of human growth hormone in *Escherichia coli*, FEBS Letters, vol. 204, No. 1, pp. 145–150 (1986).

Hsiung, et al., High Level Expression, Efficient Secretion and Folding of Human Growth Hormone in *Escherichia Coli*, Biotechnology, vol. 4, pp. 991–995 (1986).

Fraipont, et al., Engineering and overexpression of periplasmic forms of the penicillin–binding protein 3 of *Escherichia coli*, Biochem. J., vol. 298, pp. 189–195 (1994).

Stanbury, Principles of Fermentation Technology, pp. 212–215 (1984).

Lehninger, Principles of Biochemistry, pp. 128, 145, 109, 131 (Worth 1982).

Stryer, Biochemistry, 2d ed., pp. 19, 20 and 92 (Freeman 1975).

Zubay, Biochemistry, pp. 47–48, 54–56, 60–61 and 590 (Addison–Wesley 1983).

Marx, Obesity Gene Discovery May Helpm Solve Weighty Problem, Surg. Neurol., vol. 43, pp. 351–352 (1995).

McGarry, Does leptin lighten the problem of obesity? Current Biology, vol. 5, No. 12 pp. 1342–1344 (1995).

Francis, Focus on Growth Factors vol. 3, 1992, p 4–10.

```
                        SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
         (A) LENGTH: 702 base pairs
         (B) TYPE: nucleic acid
         (C) STRANDEDNESS: single
         (D) TOPOLOGY: linear (ii) MOLECULE TYPE: cDNA (iii) HYPOTHETICAL: NO
```

(iv) ANTI-SENSE: NO (xi) SEQUENCE DESCRIPTION: SEQ ID NO:1:

```
CAAGGTGCAA GAAGAAGAAG ATCCCAGGGA GGAAAATGTG CTGGAGACCC CTGTGTCGGT      60

TCCTGTGGCT TTGGTCCTAT CTGTCTTATG TTCAAGCAGT GCCTATCCAG AAAGTCCAGG     120

ATGACACCAA AACCCTCATC AAGACCATTG TCACCAGGAT CAATGACATT TCACACACGC     180

AGTCGGTATC CGCCAAGCAG AGGGTCACTG GCTTGGACTT CATTCCTGGG CTTCACCCCA     240

TTCTGAGTTT GTCCAAGATG GACCAGACTC TGGCAGTCTA TCAACAGGTC CTCACCAGCC     300

TGCCTTCCCA AAATGTGCTG CAGATAGCCA ATGACCTGGA GAATCTCCGA GACCTCCTCC     360

ATCTGCTGGC CTTCTCCAAG AGCTGCTCCC TGCCTCAGAC CAGTGGCCTG CAGAAGCCAG     420

AGAGCCTGGA TGGCGTCCTG GAAGCCTCAC TCTACTCCAC AGAGGTGGTG GCTTTGAGCA     480

GGCTGCAGGG CTCTCTGCAG GACATTCTTC AACAGTTGGA TGTTAGCCCT GAATGCTGAA     540

GTTTCAAAGG CCACCAGGCT CCCAAGAATC ATGTAGAGGG AAGAAACCTT GGCTTCCAGG     600

GGTCTTCAGG AGAAGAGAGC CATGTGCACA CATCCATCAT TCATTTCTCT CCCTCCTGTA     660

GACCACCCAT CCAAAGGCAT GACTCCACAA TGCTTGACTC AA                        702
```

(2) INFORMATION FOR SEQ ID NO:2:

(i) SEQUENCE CHARACTERISTICS:
        (A) LENGTH: 167 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:2:

```
Met Cys Trp Arg Pro Leu Cys Arg Phe Leu Trp Leu Trp Ser Tyr Leu
 1               5                  10                  15

Ser Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ala Lys Gln Arg Val Thr Gly Leu Asp Phe Ile Pro
    50                  55                  60

Gly Leu His Pro Ile Leu Ser Leu Ser Lys Met Asp Gln Thr Leu Ala
65                  70                  75                  80

Val Tyr Gln Gln Val Leu Thr Ser Leu Pro Ser Gln Asn Val Leu Gln
                85                  90                  95

Ile Ala Asn Asp Leu Glu Asn Leu Arg Asp Leu Leu His Leu Leu Ala
            100                 105                 110

Phe Ser Lys Ser Cys Ser Leu Pro Gln Thr Ser Gly Leu Gln Lys Pro
        115                 120                 125

Glu Ser Leu Asp Gly Val Leu Glu Ala Ser Leu Tyr Ser Thr Glu Val
    130                 135                 140

Val Ala Leu Ser Arg Leu Gln Gly Ser Leu Gln Asp Ile Leu Gln Gln
145                 150                 155                 160

Leu Asp Val Ser Pro Glu Cys
                165
```

(2) INFORMATION FOR SEQ ID NO:3:

(i) SEQUENCE CHARACTERISTICS:
        (A) LENGTH: 146 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:3:

```
Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30

Lys Gln Arg Val Thr Gly Leu Asp Phe Ile Pro Gly Leu His Pro Ile
        35                  40                  45

Leu Ser Leu Ser Lys Met Asp Gln Thr Leu Ala Val Tyr Gln Gln Val
50                  55                  60

Leu Thr Ser Leu Pro Ser Gln Asn Val Leu Gln Ile Ala Asn Asp Leu
65                  70                  75                  80

Glu Asn Leu Arg Asp Leu Leu His Leu Leu Ala Phe Ser Lys Ser Cys
                85                  90                  95

Ser Leu Pro Gln Thr Ser Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Val Ser Pro
130                 135                 140

Glu Cys
145
```

(2) INFORMATION FOR SEQ ID NO:4:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

```
GTTGCAAGGC CCAAGAAGCC CATCCTGGGA AGGAAAATGC ATTGGGGAAC CCTGTGCGGA      60

TTCTTGTGGC TTTGGCCCTA TCTTTTCTAT GTCCAAGCTG TGCCCATCCA AAAAGTCCAA     120

GATGACACCA AAACCCTCAT CAAGACAATT GTCACCAGGA TCAATGACAT TCACACACG      180

CAGTCAGTCT CCTCCAAACA GAAAGTCACC GGTTTGGACT TCATTCCTGG GCTCCACCCC     240

ATCCTGACCT TATCCAAGAT GGACCAGACA CTGGCAGTCT ACCAACAGAT CCTCACCAGT     300

ATGCCTTCCA GAAACGTGAT CCAAATATCC AACGACCTGG AGAACCTCCG GGATCTTCTT     360

CACGTGCTGG CCTTCTCTAA GAGCTGCCAC TTGCCCTGGG CCAGTGGCCT GGAGACCTTG     420

GACAGCCTGG GGGGTGTCCT GGAAGCTTCA GGCTACTCCA CAGAGGTGGT GGCCCTGAGC     480
```

-continued

```
AGGCTGCAGG GGTCTCTGCA GGACATGCTG TGGCAGCTGG ACCTCAGCCC TGGGTGCTGA      540

GGCCTTGAAG GTCACTCTTC CTGCAAGGAC TACGTTAAGG GAAGGAACTC TGGCTTCCAG      600

GTATCTCCAG GATTGAAGAG CATTGCATGG ACACCCCTTA TCCAGGACTC TGTCAATTTC      660

CCTGACTCCT CTAAGCCACT CTTCCAAAGG                                       690
```

(2) INFORMATION FOR SEQ ID NO:5:

(i) SEQUENCE CHARACTERISTICS:
        (A) LENGTH: 167 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:5:

```
Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

(2) INFORMATION FOR SEQ ID NO:6:

(i) SEQUENCE CHARACTERISTICS:
        (A) LENGTH: 146 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:6:

```
Val Pro Ile Gln Lys Val Gln Asp Asp Thr Lys Thr Leu Ile Lys Thr
1               5                   10                  15
```

```
Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
 50                  55                  60

Leu Thr Ser Met Pro Ser Arg Asn Val Ile Gln Ile Ser Asn Asp Leu
 65                  70                  75                  80

Glu Asn Leu Arg Asp Leu Leu His Val Leu Ala Phe Ser Lys Ser Cys
            85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Trp Gln Leu Asp Leu Ser Pro
130                 135                 140

Gly Cys
145
```

(2) INFORMATION FOR SEQ ID NO:7:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
ATGAAAAAGA CAGCTATCGC GATTGCAGTG GCACTGGCTG GTTTCGCTAC CGTAGCGCAG      60

GCC                                                                    63
```

(2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:8:

```
Met Lys Lys Thr Ala Ile Ala Ile Ala Val Ala Leu Ala Gly Phe Ala
 1               5                  10                  15

Thr Val Ala Gln Ala
            20
```

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (xi) SEQUENCE DESCRIPTION: SEQ ID NO:9:

GGGTGCTGAG GCCTTGA                                                      17

(2) INFORMATION FOR SEQ ID NO:10:

(i) SEQUENCE CHARACTERISTICS:
            (A) LENGTH: 17 base pairs
            (B) TYPE: nucleic acid
            (C) STRANDEDNESS: double
            (D) TOPOLOGY: circular (ii) MOLECULE TYPE: DNA (genomic)

(iii) HYPOTHETICAL: NO (xi) SEQUENCE DESCRIPTION: SEQ ID NO:10:

GGGTGCTGAG GCCCTGA                                                      17

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:11:

GTGCCTATCC AGAAAGTC                                                     18

(2) INFORMATION FOR SEQ ID NO:12:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (iii) HYPOTHETICAL: YES (xi) SEQUENCE DESCRIPTION: SEQ ID NO:12:

Val Pro Ile Glu Lys Val
1               5

(2) INFORMATION FOR SEQ ID NO:13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (xi) SEQUENCE DESCRIPTION: SEQ ID NO:13:

TCCCAAGCTT TCAGCATTCA GGGCTAAC                                          28

(2) INFORMATION FOR SEQ ID NO:14:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:14:

GTGCCCATCC AAAAAGTC                                                      18

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:15:

TCCCAAGCTT TCAGCACCCA GGGCTGAG                                           28
```

PEGYLATED OBESE (OB) PROTEIN COMPOSITIONS

This application is a continuation-in-part of application Ser. No. 08/484,629, filed Jun. 7, 1995 which is a continuation-in-part of application Ser. No. 08/435,777 filed May 5, 1995. BACKGROUND Obesity is reported to be the commonest nutritional disorder in Western societies (Zhang, Y. et al. (1994)) More than three in 10 adult Americans weigh at least 20% in excess of their ideal weight (Zhang, Y. et al (1994)). Increased body weight is a public health problem because it is associated with important medical morbidities such as type II diabetes mellitus (i.e., non-insulin-dependent diabetes mellitus), hypertension and hyperlipidaemia (Crundy, S. M. & Barnett (1990)). There is evidence that body weight is physiologically regulated and the obesity (and its related conditions or diseases) are due in part to derangements in this regulation (Zhang, Y. et al. (1994)).

In rodents, there are described seven single gene mutations that result in an obese phenotype; five of which are present in mice. Of these seven rodent models, one of the most intensively studied is the obese (ob) gene mutation in mice, identified in 1950 (Ingalls, A. M. et al. (1950)). Mice homozygous for this ob gene mutation are profoundly obese, develop type II diabetes mellitus, and are hyperphagic and hypometabolic, as part of a syndrome resembling morbid obesity in man (Friedman J. M. et al. (1991)). This ob gene is mapped to the mouse proximal chromosome 6 and encodes a protein (i.e., ob protein) expressed in adipose tissue (Zhang, et al. (1994)). Mice homozygous for the ob gene mutation have little to no production of this ob protein, and accordingly have defective regulation of body weight leading to obesity.

The murine or human ob proteins may be administered to patients suffering from defects or mutations in their corresponding obese (ob) gene, which defects or mutations prevent or interfere with the production and/or function of the ob proteins in modulating body weight. These proteins may therefore be used as a hormone-like substance to control, prevent or treat obesity and its related diseases and conditions in man and animals.

To use the murine or human ob proteins in this manner, these proteins can be administered through injection by a variety of routes, such as intraperitoneal, intravenously, intramuscularly or subcutaneously, in frequent dosages. Since it is administered frequently through injection, it is important that the murine or human ob proteins be purified, preferably to homogeneity, be free of contaminating protein materials, and be recombinantly expressed in a soluble and biologically active form. It is generally known to practitioners in the field that contaminants present in injectable medication can often lead to toxic side-effects or adverse immunological responses.

While the murine ob gene sequence is disclosed in Zhang, et al (1994), no methods of expressing the murine ob protein or its human counterpart have been reported, much less producing these proteins in a biologically active and soluble state from which the proteins can be purified to homogeneity. Therefore it is important, and is an object of this invention, to express and produce the murine or human ob proteins in a homogeneous, soluble, and biologically-active state.

SUMMARY OF THE INVENTION

It has been discovered that recombinant human and murine ob proteins can be expressed in a biologically active and soluble state, and thereafter purified to homogeneity suitable for injection to patients for treating, preventing or controlling obesity and its related conditions and diseases, such as type II diabetes mellitus, hypertension, hyperlipidaemia and the like.

In accordance with this invention, the human and murine ob proteins can be produced recombinantly in a biologically active form and purified to homogeneity by first constructing novel expression vectors for *Escherichia coli* (*E. coli*). These expression vectors contain a promoter and a DNA sequence, which DNA sequence encodes a fusion protein comprising two parts: the signal peptide of the outer membrane protein A of *E. coli* (i.e., sOmpA) and the human or murine ob protein. In accordance with this invention, the next step for producing the biologically active recombinant form of the murine and human ob proteins is to insert this expression vector in an *E. coli* host whereby there is obtained efficient expression and translocation of the fusion protein into the periplasmic space (i.e., between the inner and outer cell membranes of the *E. coli* microorganism), at which point the signal peptide is excised from the ob protein leaving the ob protein in a soluble and biologically active form.

The present invention is further directed to 1) an expression vector containing the DNA encoding a fusion protein comprising a sOmpA signal peptide and a human or murine ob protein; 2) to a host organism transfected or transformed by such expression vector; and 3) to the DNA sequence encoding the human ob protein and 4) polyethylene or polypropylene glycol conjugates of the ob protein.

DETAILED DESCRIPTION OF THE INVENTION

Figure 1:
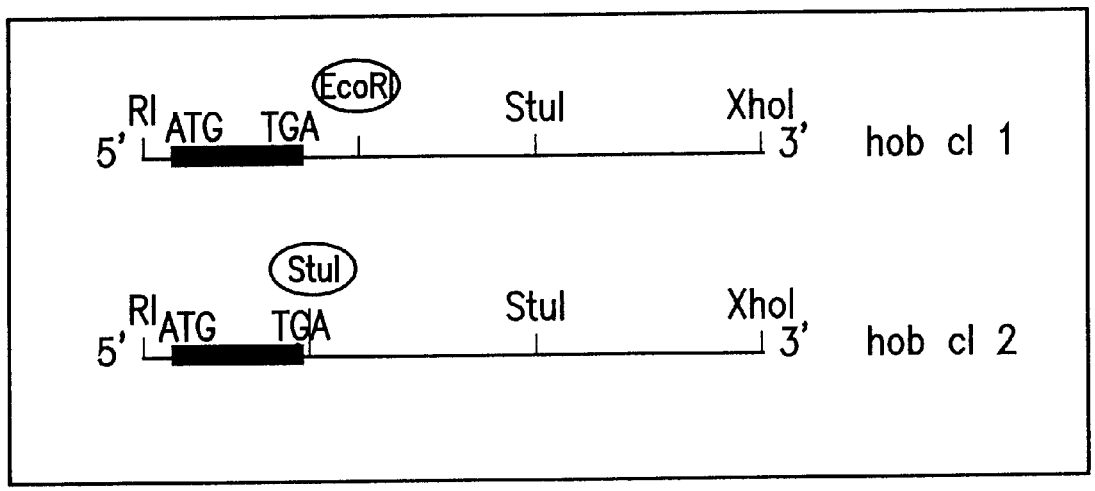
FIG. 1 is a schematic of the two clones for human ob protein; i.e., hob1 and hob2, which schematics depict the location and types of restriction sites located at the 5' and 3' ends of the human ob cDNA sequence.

It has been discovered a method for expressing recombinant human and murine ob proteins in a biologically active and soluble state, and for producing these proteins in a purified homogeneous form suitable for administration to animals and humans. The recombinant human and murine ob proteins of this invention can be conjugated with polyethylene or polypropylene glycol homopolymers.

The human and murine ob proteins can be produced recombinantly in a biologically active state in accordance with this invention by first constructing novel expression vectors for *E. coli* containing a promoter and a DNA sequence, which DNA sequence encodes a fusion protein comprising the signal peptide of the outer membrane protein A of *E. coli* (i.e., sompA) and the human or murine ob protein. The next step for obtaining the murine or human ob protein in a biologically active and soluble form is to insert this expression vector in an E. coli host whereby there is obtained efficient expression and translocation of the fusion protein into the periplasmic space (i.e., between the inner and outer cell membranes of the E. coli). Once in the periplasmic space, the signal peptide is excised from the ob protein leaving the ob protein in a soluble and biologically active form. Next, the ob proteins are efficiently secreted in soluble and biologically active form into cell free medium following treatment of the host E. coli cells to cold osmotic shock, at which point the ob proteins are purified to homogeneity by the sequential use of anion exchange chromatography, hydrophobic interaction column chromatography and gel filtration, carried out in that order.

Murine Ob Gene and Murine Ob Protein

The method for expressing and producing the murine ob protein in accordance with this invention is achieved utilizing the murine ob gene as reported by Zhang et al (1994), the sequence for which gene is a 702 base pair (bp) nucleotide sequence identified herein as SEQ ID NO. 1. This murine ob gene sequence comprises a 501 bp coding sequence or open reading frame (ORF) starting with a start codon at nucleotide 36 and terminating with a stop codon at nucleotide 537, and having untranslated sequences at both the 31 and 5' ends. The ORF contains a 63 bp signal sequence from nucleotide 36 to 98.

This murine ob gene sequence (SEQ ID NO: 1) encodes the murine ob protein (plus its signal sequence) whose amino acid sequence is 167 amino acids in length and is identified as SEQ ID NO: 2. In this protein of SEQ ID NO: 2, the first 21 amino acids represent the signal sequence of the murine ob protein. The mature murine ob protein (without its signal sequence) extends from amino acid 22 (Val) to amino acid 167 (Cys) and is represented by SEQ ID NO: 3.

The Human Ob Gene and Human Ob Protein

The method for expressing and producing the human ob protein in accordance with this invention is achieved utilizing the human ob gene, the sequence for which gene is a 690 bp nucleotide sequence identified herein as SEQ ID NO: 4.

Zhang et al (1994) reports the human ob gene as highly homologous to the murine ob gene, and discloses a conventional method using oligonucleotide probes directed to the murine ob gene which can be utilized to 1) screen a cDNA library of clones derived from human adipose tissue, 2) identify those clones having the human ob gene, and 3) isolate and sequence the human ob gene sequence. When sequenced by conventional means, this human ob gene sequence is determined to have the nucleotide sequence SEQ ID NO: 4.

As with the murine ob gene, the human ob gene comprises a 501 bp coding sequence or open reading frame (ORF) starting with a start codon at nucleotide 37 and terminating with a stop codon at nucleotide 538, and having an untranslated sequences at both the 3' and 5' ends. The ORF contains a 63 bp signal sequence from nucleotide 37 to 99.

This human ob gene sequence (SEQ ID NO: 4) encodes a human ob protein plus its signal sequence whose amino acid sequence of 167 amino acids in length is identified as SEQ ID NO: 5. The first 21 amino acids of this protein of 167 amino acids in length represent the signal sequence. The mature human ob protein (without its signal sequence) extends from amino acid 22 (Val) to amino acid 167 (Cys) and is represented by SEQ ID NO: 6.

Zhang et al (1994) reports 84% identity between the murine and human ob proteins. Zhang et al (1994) also reports that variants of the murine and human proteins exist, one such variant being characterized in both species by a deletion of glutamine 49. Approximately 30% of cDNA clones in the libraries derived from mouse adipose tissue and human adipose tissue have the codon 49 missing (Zhang et al (1994)).

Definitions

The following terms shall have the definitions set out below:

Murine ob protein (mob) refers to the protein of SEQ ID NO: 3 whose biological properties relate to the treating, controlling or preventing obesity or its associated conditions and diseases. Specifically, a murine ob protein is defined to include any protein or polypeptide having an amino acid sequence which is substantially homologous to the amino acid sequence SEQ ID NO: 3, and further having the following biological activities:

1) When the protein or polypeptide is administered by intracerebroventricular (ICV) injection to 16–18 hour fasted mature obese ob/ob mice having a body weight of at least 30 grams at a dose of 20 ug or less using the methods of Haley and McCormick (1957), the protein or polypeptide:
   (a) reduces food intake during a 5 hour feeding test by 50% compared to vehicle injected control mice (ED50 for reducing food intake); and
   (b) reduces body weight gain during the 24 hours following the ICV injection by at least 50% compared to vehicle injected control mice (ED50 for reducing body weight gain);

or

2) When the protein or polypeptide is administered intraperitoneal (IP) to non-fasted mature ob/ob mice having a body weight of at least 30 grams twice a day at the beginning of daylight and again at the 3 hour point of the dark phase, for one week, in a total daily dose of 20 ug or less, the protein or polypeptide:
   (a) reduces 5 and 24 hour food intake by at least 20% compared to vehicle injected control mice (ED20 for reducing food intake); and
   (b) reduces body weight gain during the 24 hours following the first IP injection by at least 20% compared to vehicle injected control mice (ED20 for reducing body weight gain).

As used herein the term murine ob protein includes such proteins modified deliberately, as for example, by site directed mutagenesis or accidentally through mutations.

Human ob protein (hob) refers to the protein of SEQ ID NO: 6 whose biological properties relate to the treating, controlling or preventing obesity or its associated conditions and diseases. Specifically, a human ob protein is defined to include any protein or polypeptide having an amino acid sequence which is substantially homologous to the amino acid sequence SEQ ID NO: 6, and further having the following biological activities:

1) When the protein or polypeptide is administered ICV to 16–18 hour fasted mature obese ob/ob mice having a body weight of at least 30 grams at a dose of 20 ug or less using the methods of Haley and McCormick (1957), the protein or polypeptide:
   (a) reduces food intake during a 5 hour feeding test by 50% compared to vehicle injected control mice (ED50 for reducing food intake); and
   (b) reduces body weight gain during the 24 hours following the ICV injection by at least 50% compared to vehicle injected control mice (ED50 for reducing body weight gain);
or
2) When the protein or polypeptide is administered IP to non-fasted mature ob/ob mice having a body weight of at least 30 grams twice a day at the beginning of daylight and again at the 3 hour point of the dark phase, for one week, in a total daily dose of 20 ug or less, the protein or polypeptide:
   (a) reduces 5 and 24 hour food intake by at least 20% compared to vehicle injected control mice (ED20 for reducing food intake); and
   (b) reduces body weight gain during the 24 hours following the first IP injection by at least 20% compared to vehicle injected control mice (ED20 for reducing body weight gain).

As used herein the term human ob protein includes such proteins modified deliberately, as for example, by site directed mutagenesis or accidentally through mutations.

Substantially homologous which can refer both to nucleic acid and amino acid sequences, means that a particular subject sequence, for example, a mutant sequence, varies from a reference sequence by one or more substitutions, deletions, or additions, the net effect of which do not result in an adverse functional dissimilarity between the reference and subject sequences. For purposes of the present invention, sequences having greater than 95 percent homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characteristics are considered substantial quivalents. Generally, homologous DNA sequences can be identified by cross-hybridization under standard hybridization conditions of moderate stringency.

Fragment of the murine or human ob protein means any protein or polypeptide having the amino acid sequence of a portion or fragment of a murine or human ob protein, and which has the biological activity of the murine or human ob protein, respectively. Fragments include proteins or polypeptides produced by proteolytic degradation of the murine or human ob proteins or produced by chemical synthesis by methods routine in the art.

An ob protein or fragment thereof is biologically active when administration of the protein or fragment to a mammal, including man, reduces food intake and reduces the rate of weight gain in the mammal. Determining such biological activity of the human or murine ob protein can caried out by conventional, well known tests utilized for such purposes on one or more species of mammals, particularly the obese ob/ob mouse. Several of these tests which can be utilized to demonstrate such biological activity are described herein. In determining biological activity in accordance with the ICV test in ob/ob mice as described herein, the human or murine ob protein preferably has an ED50 for reducing food intake of 20 ug or less and an ED50 for reducing body weight gain of 20 ug or less. Alternatively, in determining biological activity of the human or murine ob protein in accordance with the IP test in ob/ob mice as described herein, the human or murine ob protein preferably has an ED20 for reducing food intake of 20 ug or less and an ED20 for reducing body weight gain of 20 g or less. Generally, fragments which exhibit the above mentioned biological activity are preferred.

Replicon is any genetic element (e.g., plasmid, chromosome, virus) that functions as an autonomous unit of DNA replication in vivo, i.e., capable of replication under its own control.

Expression vector is a replicon, such as a plasmid, phage or cosmid, to which another DNA segment may be attached so as to bring about the replication of the attached segment. It comprises a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences.

Clone is a group of DNA molecules derived from one original length of DNA sequences and produced by a bacterium or virus using genetic engineering techniques, often involving plasmids.

Signal sequence is the nucleic acid sequence located at the beginning (5' end) of the coding sequence of a protein to be expressed. This signal sequence encodes a signal peptide, N-terminal to the newly synthesized protein, that directs the host cell to translocate the protein toward or through the host cell membrane, and which signal peptide is usually excised during such translocation.

Start codon is a codon usually ATG located in the coding sequence of a protein, and usually at the 5' end, and signals the first amino acid in a protein sequence.

Stop codon is a nonsense codon located in and usually at the 3' end of a coding sequence of a protein, and signals the end of a growing polypeptide chain.

Open Reading Frame (ORF) is a linear array of codon triplets in double-stranded DNA encoding an amino acid sequence in a cell in vitro or in vivo when placed under the control of appropriate regulatory sequences. The boundaries of the ORF are determined by a start codon at the 5' terminus and a stop codon at the 3' terminus. It may be referred to as a "coding sequence".

Promoter sequence is DNA regulatory region capable of binding RNA polymerase in a cell and initiating transcription of a downstream (3' direction) open reading frame of one or more structural genes. The promoter sequence is usually located at the 5' end of the signal sequence or open reading frame and extends upstream in the 5' direction to include the minimum number of bases or elements necessary to initiate transcription of the polypeptide at a level detectable above background.

A coding sequence or ORF is under the control of a promoter sequence when RNA polymerase transcribes the coding sequence into mRNA.

A composition comprising A (where A is a single polypeptide) is homogeneous for A when there is no detectable quantity of contaminating proteins or other endogenous materials, as detected by conventional means, for example, staining of polyacrylamide gels. For purposes of this invention, the term homogeneous shall refer to a composition comprising a single protein or polypeptide when at least 95% by weight of the composition is that single protein or polypeptide.

Method for Expressing Ob Proteins

The following steps outline the methods for recombinantly expressing the human and murine ob proteins in a biologically active and soluble cell-free state, free of other mammalian proteins, from which the ob proteins can then be purified to homogeneity. These steps are exemplified in detail in the examples.

1) Obtaining the Mouse and Human Ob Genes

The cDNA (SEQ ID NO. 1) encoding the murine ob protein plus its natural signal sequence is published in Zhang et al. (1994). This murine cDNA has been isolated and amplified by PCR technique using oligodeoxynucleotide DNA primers by conventional techniques. These DNA primers and the methods for obtaining them are described in Zhang et al (1994).

The cDNA (SEQ ID NO. 4) encoding the human ob protein plus its natural signal sequence is obtained using the same oligodeoxynucleotide DNA primers as used in Zhang et al (1994) to obtain the murine ob gene. By using conventional technique, this human cDNA has been isolated from a lambda phage cDNA library made from RNA derived from human adipocyte tissue.

The human or mouse ob cDNA may be obtained not only from cDNA libraries, but by other conventional means; e.g., by chemical synthesis, or by cloning genomic DNA, or fragments thereof, purified from the desired cell. These procedures are described in Sambrook, et al. (1989), *DNA Cloning: A Practical Approach* (1985), Benton and Davis (1977), and Grunstein and Hogness (1975). To obtain the human or mouse ob cDNA from cDNA libraries, the cDNA libraries are screened by conventional DNA hybridization techniques by the methods of Benton and Davis (1977) or Grunstein and Hogness (1975) using primers prepared by reverse transcription of polyadenylated RNA isolated from murine adipose cells containing the murine ob gene. Clones which hybridize to the primers are analyzed by restriction endonuclease cleavage, agarose gel electrophoresis, and additional hybridization experiments ("Southern blots") involving the electrophoresed primers. After isolating several clones which hybridized to the murine cDNA probes, the hybridizing segment of one clone is subcloned and sequenced by conventional techniques.

Clones derived from genomic DNA may contain regulatory and intron DNA regions in addition to coding regions: clones derived from cDNA will not contain intron sequences. In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Whatever the source, the human or murine ob gene may be molecularly cloned into a suitable vector for propagation of the gene by methods known in the art. Any commercially available vector may be used. For example, the mouse cDNA may be inserted into a pCDNA3 vector and the human cDNA may be inserted into a pBluescriptSK⁻ vector. Appropriate vectors for use with bacterial hosts are described by Pouwels, et al (1985). As a representative but nonlimiting example, useful cloning vectors for bacterial use can comprise a selectable marker and bacterial origin of replication derived from commercially available plasmids which are in turn derived from the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wisc., USA).

The nucleotide sequences of the human or murine ob gene inserted in these commercially available vectors can be verified by methods known in the art, by standard nucleotide sequencing techniques.

Other nucleic acids that code for ob proteins of species other than human or murine may be used herein. Accordingly, while specific DNA has been cloned and sequenced in relation to the human and mouse ob gene, any animal adipocyte potentially can be used as the nucleic acid source of the ob protein.

2) Construction of an Expression Vector for the Human and Murine Ob Protein

The human or murine ob gene cloned in accordance with the methods described above are used to construct the expression vectors for the human and murine ob proteins, respectively.

For expression of the biologically active human and murine ob protein by a transfected or transformed *E. coli* host cell and for secretion of the ob protein into the periplasm, a novel expression vector can be utilized. This expression vector includes a promoter and a DNA sequence encoding a fusion protein. The fusion protein consists of two parts: the first part being a signal peptide for the outer membrane protein A of *E. coli* (sOmpA) and the second part of the fusion protein being the human or murine ob protein (minus their own natural signal sequences). The DNA sequence encoding this fusion protein also consists of two parts: a first part that encodes the sOmpA peptide and a second part that encodes the murine or human ob protein (minus their natural signal sequences). The first part of the DNA sequence that encodes the sOmpA peptide is the signal sequence described by De Sutter, K. et al (1994) and has the nucleotide sequence of SEQ ID NO: 7. The second part of the two-part DNA sequence encodes the murine or human ob proteins and has the nucleotide sequence of SEQ ID NO: 1 or SEQ ID NO: 4, respectively minus that portion of the nucleotide sequence that encodes the respective natural signal sequences.

The signal peptide encoded by the sOmpA signal sequence of SEQ ID NO: 7 has the amino acid sequence SEQ ID NO: 8 as reported by De Sutter, K. et al (1994).

The novel expression vector of this invention is achieved by inserting the promoter and DNA sequence encoding the fusion protein into a conventional expression vector suitable for expression of recombinant proteins in E. coli host cells.

In constructing this novel expression vector in accordance with this invention, any promoter may be used as long as it is capable of controlling transcription of the fusion protein comprising the sOmpA peptide and the ob protein in the E. coli host cell. When the sOmpA is used as the signal peptide, it is preferable to use both the lac-operator promoter ($PO_{lac}$) and the lipoprotein promoter ($P_{lpp}$). Other useful promoters for such expression in E. coli include the T7 RNA polymerase promoter described by Studier et al, (1986), the lacz promoter described by Lauer, (1981) and available as ATCC 37121, the tac promoter described by Maniatis, (1982) and available as ATCC 37138, the alkaline phosphatase (phoA) promoter, and the trp promoter described by Goeddel et al. (1980). Other promoters have been discovered and utilized in E. coli and details concerning their nucleotide sequences, enabling a skilled worker to ligate them functionally within the expression vector of this invention, have been published (Siebenlist et al.(1980).

Figure 2:
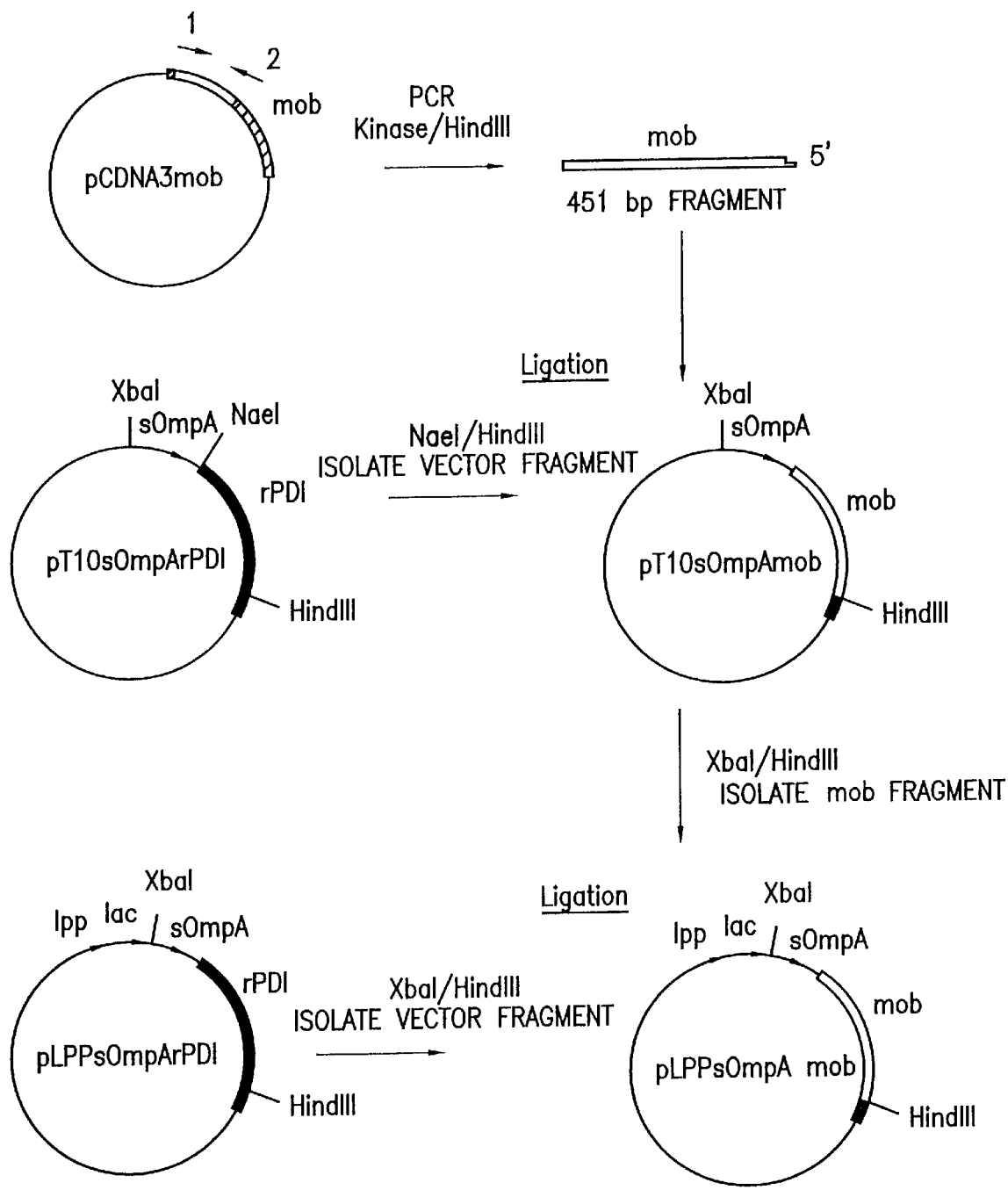
FIG. 2 is a schematic of the construction of the pLPP-sOmpA mob expression vector.

Next, the method for constructing this novel expression vector is described. This method is further detailed in the Examples and depicted in FIGS. 1 and 2. First, the coding sequence of the human or mouse ob gene (minus its natural signal sequence) is incorporated into a plasmid containing the sOmpA signal sequence, such as the plasmid pT10sOmpArPDI. This pT10sOmpArPDI plasmid and its construction and preparation is described by De Sutter K. et al (1994). Once incorporated into this plasmid, the human or mouse ob gene is fused to this sOmpA gene to create a "hybrid gene sequence" in this plasmid. The sOmpA gene must be upstream of the 5' region of the ob gene coding sequence. Thereafter, promoters as enumerated above, and preferably the lipoprotein promoter ($P_{lpp}$) and the lac promoter-operator ($PO^{lac}$), are incorporated into this plasmid containing the hybrid gene sequence to create the expression vectors of this invention. Two embodiments of these expression vectors are identified as pLPPsOmpA mob and pLPPsOmpA hob1 and are depicted in FIGS. 1 and 2, respectively.

Any method or procedure known in the art to construct such a plasmid may be used. Moreover, the order by which one fuses the sOmpA and ob gene sequences, incorporates the gene sequences into a suitable plasmid, and incorporates the promoter to arrive at the expression vector of this invention is not critical. For example, the sOmpA gene sequence can be initially fused to the murine or human ob gene sequence directly to create a hybrid gene sequence, and then this hybrid sequence inserted into a plasmid having already incorporated therein the appropriate promoters. It is necessary however that the sOmpA gene sequence be upstream at the 5' end of the murine or ob gene sequence.

We have discovered that by using such novel expression vector, and in particular, by using the signal sequence encoding the sOmpA, the murine or human ob proteins can be translocated to the periplasmic space, where the signal peptide is appropriately cleaved leaving intact the human or murine ob proteins therein in a soluble and biologically active form. Once in this periplasmic space, the ob proteins are efficiently secreted to the cell free environment free of other mammalian proteins upon subjecting the host cells to cold osmotic shock, at which time the ob proteins can be purified to homogeneity in a biologically active form.

3. Expressing the Human or Murine Ob Proteins in Transformed E. coli cells

Next, the expression vectors constructed in accordance with the above described procedures are inserted into a host E. coli cell to transform the E. coli cell. Any strain of E. coli may be used, such as E. coli K-12 strain 294 as described in British Patent Publication No. 2055382 A (ATCC No. 31446). Other strains useful in accordance with this invention include E. coli MC1061 (Casadaban and Cohen (1980)), E. coli B, E. colix1776 (ATTC No. 31537), and E. coli W 3110 (ATCC No. 27325) or other strains many of which are deposited and available from recognized microorganism depository institutions.

The transformed E. coli cells are grown to an appropriate cell density and cultured by standard methods. In so growing and culturing the transformed E. coli hosts, the expression vectors of this invention efficiently and effectively allow expression of the murine or human ob proteins and translocation of these same proteins into the periplasm of the host E. coli cells in a soluble and biologically active form. The sOmpA signal peptide (i.e., part 1 of the fusion protein) is cleaved during translocation of the fusion protein into the periplasm yielding the biologically active ob protein free of other mammalian proteins or polypeptides.

Methods for Purifying Human or Murine Ob Proteins

The recombinantly produced human or murine ob proteins in a soluble biologically active state in the periplasm of transformed E. coli cells are thereafter purified to homogeneity.

1) Obtaining Human or Murine Ob Protein in a cell-free State Free of other Mammalian Proteins or Polypeptides.

The recombinant human and murine ob proteins translocated to the cell periplasm in accordance with the procedures described herein can be effectively secreted outside the cell by subjecting the host cells to cold osmotic shock by methods known in the art and described by Koshland, D. and Botstein, D. (1980). The use of cold osmotic shock liberates from the E. coli the ob proteins in their biologically active state free of other mammalian proteins or polypeptides.

2) Purification to Homogeneity of Human or Murine Ob Proteins

The human or murine ob proteins located in the osmotic fluid following cold osmotic shock of transformed E. coli cells, in accordance with the above described procedure, are biologically active and can be purified to homogeneity using a combination of anion exchange column chromatography, hydrophobic interaction column chromatography and gel filtration. Anion exchange and hydrophobic interaction chromatography can be carried out in any order, however, the use of either must precede gel filtration.

The anion exchange stage can be carried out by conventional means. The preferred column for anion exchange chromatography is a Q Sepharose Fast Flow column. Suitable anion exchange chromatography media include various insoluble matrices comprising diethylaminoethyl (DEAE) or diethyl-(2-hydroxypropyl)aminoethyl (QAE) groups. The matrices can be acrylamide, agarose, dextran, cellulose or other types commonly employed in protein purification. A particularly useful material for anion exchange chromatography is DEAE-Sephacel Sephacel (Pharmacia). When media containing DEAE groups are employed, extracts containing murine or human ob proteins are applied at a weakly basic pH; e.g., pH 8.1. The bound murine or human ob proteins can be eluted in more highly purified form by application of a salt gradient in a suitable buffer such as Tris-HCl. Generally, the characteristics of the gradient can be determined by preliminary elution experiments involving a small quantity of recombinant protein.

The material containing the human or murine ob protein obtained through the use of anion exchange chromatography, when anion exchange chromatography is used as the first stage of purification, is next subjected to hydrophobic interaction chromatography. Hydrophobic interaction chromatography is a separation technique in which substances are separated on the basis of differing strengths of hydrophobic interaction with an uncharged bed material containing hydrophobic groups. Typically, the hydrophobic interaction column is first equilibrated under conditions favorable to hydrophobic binding, e.g., high ionic strength. A descending salt gradient may be used to elute the sample.

Any hydrophobic interaction column can be used. The preferred hydrophobic column is phenyl Sepharose; however butyl Sepharose can also be utilized. In accordance with the invention, the material containing the recombinant murine or human ob protein which has been eluted from the anionic column is loaded onto a column containing a relatively strong hydrophobic gel such a phenyl sepharose. To promote hydrophobic interaction with the hydrophobic gel, a solvent is used which contains, for example, greater than or equal to 0.4 M ammonium sulfate, with 0.4 M being preferred. Thus the column and the sample are adjusted to 0.4 M ammonium sulfate in 50 mM Tris buffer and the sample applied to the column. The column is washed with 0.4 M ammonium sulfate buffer. The ob protein is then eluted with solvents which attenuate hydrophobic interactions such as, for example, decreasing salt gradients, ethylene or propylene glycol, or urea. A preferred embodiment involves washing the column sequentially with the Tris buffer and the Tris buffer containing 20% ethylene glycol. The ob protein is subsequently eluted from the column with a gradient of decreasing ammonium sulfate concentration and increasing ethylene glycol concentration in the Tris buffer. The collective and sequential use of anion exchange chromatography and hydrophobic interaction column chromatography, in any order, yields human or murine ob protein routinely at an estimated purity of 90%.

The gel filtration chromatography step follows the anion exchange chromatography and hydrophobic interaction column chromatography steps outlined above, and can be performed by any conventional gel filtration procedure. The ob protein eluted from the hydrophobic interaction column, or the anion exchange column, whichever column is used last, can be concentrated and dialyzed to a small volume by using a membrane with a cut-off molecular weight of 10,000 (AMICONYM10 membrane). The concentrated material can then be loaded onto a column containing gel filtration media such as G100-Sephadex (Pharmacia). The ob protein can then be separated from other contaminants on the basis of its molecular weight by standard techniques using SDS-PAGE.

The collective and sequential use of anion exchange chromatography, hydrophobic interaction column chromatography and gel filtration routinely yields human or murine ob protein at 95% purity.

3) Sequence Analysis N terminal amino acid sequencing of the purified murine or human ob protein can be performed by methods known in the art; e.g., by electrotransfer according to the methods of Laemli, U. K. (1970) or by the procedures described by Matsudaira, P., (1987). Internal sequencing can also be done by methods known in the art. For example, peptide fragments may be generated by digesting the M band (on nitrocellulose) with endoproteinase Lysine C and then separated by an HPLC system.

Biological Assays for Human or Murine Ob Proteins

The biological activity of the purified human and murine ob proteins of this invention are such that frequent administration of the ob protein by injection to human patients or mice result in decreased food intake and decreased rate of weight gain compared to non-injected or control groups of subjects.

The biological activity of the human and murine ob proteins, or fragments thereof, obtained and purified in accordance with this invention can be tested by routine methods; e.g., by repeated or single intracerebroventricular (ICV) injection in ob/ob mice according to the procedures of Haley, T. J. et al (1957) as described in detail in Example 10. Based on this ICV test, the ED50 for reducing food intake and the ED50 for reducing body weight gain can be determined. In addition, the biological activity of the purified human and murine ob proteins or fragments thereof can be determined by repeated IP injection in ob/ob mice as detailed in Example 11. Based on the IP test, the ED20 for reducing food intake and the ED20 for reducing body weight gain can be determined.

The biological activity of the human and murine ob proteins, or fragments thereof, obtained and purified in accordance with this invention can also be determined in humans by methods known in the art; e.g., measuring the reduction of test meal intake following IV administration of the ob protein to the obese human test subjects compared to IV administration of saline control, in accordance with the methods of Muurahainen, N. E., et al (1991), and as described in detail in Example 12. Alternatively, the ability of the purified murine and human ob proteins of this invention to reduce the rate of weight gain (e.g., induce weight loss) can be determined by repeated IV administration to obese human test subjects according to the methods of Drent, M. L. et al (1995), as described in detail in Example 13.

The murine and human ob proteins of this invention when purified in accordance with this invention have biological activity in that:

1) When they are administered by intracerebroventricular (ICV) injection to 16–18 hour fasted mature obese ob/ob mice having a body weight of at least 30 grams at a dose of 20 ug or less using the methods of Haley and McCormick (1957), the protein or polypeptide:
 (a) reduces food intake during a 5 hour feeding test by 50% compared to vehicle injected control mice (ED50 for reducing food intake); and
 (b) reduces body weight gain during the 24 hours following the ICV injection by at least 50% compared to vehicle injected control mice (ED50 for reducing body weight gain);
and
2) When they are administered intraperitoneal (IP) to non-fasted mature ob/ob mice having a body weight of at least 30 grams twice a day at the beginning of daylight and again at the 3 hour point of the dark phase, for one week, in a total daily dose of 20 µg or less, the protein or polypeptide:
 (a) reduces 5 and 24 hour food intake by at least 20% compared to vehicle injected control mice (ED20 for reducing food intake); and
 (b) reduces body weight gain during the 24 hours following the first IP injection by at least 20% compared to vehicle injected control mice (ED20 for reducing body weight gain).

In addition this reduction in body weight and food intake even take places at doses below 20 ug or less, even at a dosage level administered ICV of 1 µg or less especially when these proteins are purified to homogenity.

The biological assays described above and detailed in the examples for determining the biological activity of human and/or murine ob proteins can be used to determine the biological activity of fragments of these proteins, whether these fragments are produced by proteolytic degradation of the ob proteins, by chemical synthesis by recombinant protein expression of a portion DNA sequence for the OB proteins or by any other means known to the skilled artisan.

In accordance with an embodiment of this invention, the murine and human OB protein of this invention can be conjugated with polyethylene or polypropylene glycol homopolymers which can be unsubstituted or substituted by etherification of the one of the hydroxy groups at one of its ends with a lower alkyl group. These conjugates provide the OB protein in stable form and improve the half life of these proteins. In addition, the use of these conjugates formed from polyethyleneglycol or polypropylene glycol homopolymers provide means for increasing the half life of the activity of the OB protein in the body. Furthermore, these conjugates have been found to provide additional advantages such as increasing the stability and circulation time of the therapeutic OB protein in the body while also decreasing the immunogenicity of the OB protein. These pegylated OB proteins can also be readily adsorbed in the human body and provide increased uptake in the blood system.

The preferred polyethylene or polypropylene glycol homopolymers which are conjugated to the OB protein have molecular weights of approximately 15 to 60 kDa, to produce a protein which can be mono- or poly-pegylated with polyethylene or polypropylene glycol molecules. In the preferred case, the OB protein is either mono- or di-pegylated to form a conjugate with polyethylene or polypropylene glycol units, which units in the conjugate have a total molecular weight of from 15 to 60 kDa, most preferably from 35 to 45 kDa. In general, the conjugates are produced as mixture of polyethylene and polypropylene glycol conjugates since polyethylene and polypropylene glycol starting materials are sold as a mixture of different homopolymers having different molecular weights. The molecular weight set forth above is average molecular weight of the mixture of OB conjugates thus produced. These mixtures can be separated into the individual conjugates, if desired, by conventional means such as by column chromatography which includes HPLC. However, for treatment, generally this conjugate is utilized as a mixture The polyethyleneglycol or polypropylene glycol polymers [PEG] can be attached to the OB protein via the free N-terminal amino acid of the protein to form the conjugate by any conventional means. Methods for attachment of the polyethylene or polypropylene glycol to form the conjugates with the OB protein can be by any of the many number of known methods available. The polyethylene or polypropylene glycol may be covalently bonded through the N-terminal amino acid of the protein, as well as also through the various lysine residues on the OB protein.

Additionally, the polyethyene or polypropylene glycol homopolymers may be conjugated to the OB protein by bi- or poly functional linking groups. In producing mono-polyethylene or polyproplylene gylcol homopolymer conjugates, di-functional linkers are used and the homopolymer is conjugated to one functional group of this linker whereas the N-terminal amino acid as well as the lysine group of the OB protein can be conjugated to the other functional group of this linker. Tri- or poly- [polyethylene or polypropylene glycol] polymers, conjugates with the OB protein are formed by using a tri-functional or poly-functional linker. The homopolymer can be conjugated to two or more of these functional groups with one remaining functional group of the linker being attached to the OB protein. Among these linkers are those poly-functional linkers having amine and carboxy functional groups. Amine groups can conjugate with the functionalized hydroxy group of the polyethylene or polypropylene glycol to form an amide linkage. Carboxy groups can conjugate with the amine groups on the OB protein to form an amide bond and with the functionalized hydroxy group on the glycol to form an ester. Among the many types of linking groups which can be utilized to form the conjugate between the OB protein and the PEG are those disclosed in U.S. Pat. No. 4,902,502, Nitecki; U.S. Pat. No. 5,034,514, Nitecki; U.S. Pat. No. 4,609,546, Hiratani; U.S. Pat. No. 5,122,614, Zalipsky; and U.S. Pat. No. 4,847,325, Shadle.

In accordance with an especially preferred embodiment of this invention are those conjugates of the formula

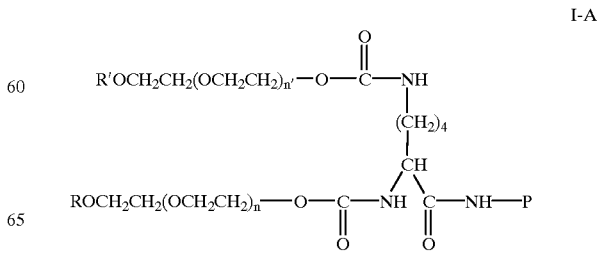

I-A

-continued

I-B

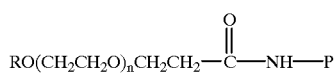

where P is the murine or human OB protein described herein; and n and n' are an integers whose sum is from 300 to 1200 so that the average molecular weight of all PEG units is from 15 to 60 kDa and the total molecular weight of the conjugate is from 30 kDa to 80 kDa; and R and R' are lower alkyl.

The compound of formula I-A and I-B can be prepared from the known polymeric materials

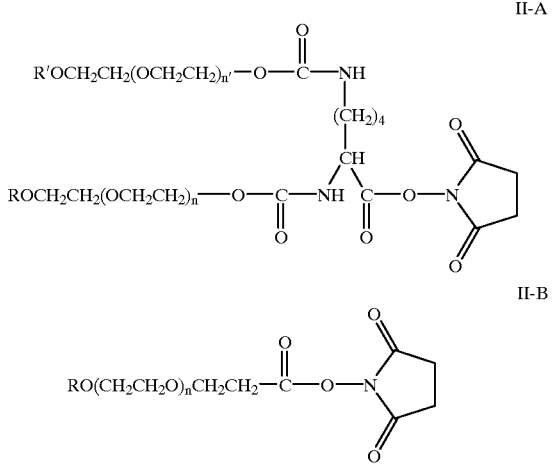

by condensing them with the murine or human OB protein of this invention. Any conventional method of reacting an activated ester with an amine to form an amide can be utilized. In the reaction illustrated above, the exemplified succinimidyl ester is a leaving group causing the amide formation. Where the compound of formula II-B is utilized to produce the compound of formula I-B, the reaction with the murine or human OB protein of this invention is carried out in the same manner described in connection with the conversion of the compound of formula II-A to the compound of formula I-A. These succinimidyl ester such as the compound of formula II-A to produce conjugates with proteins are disclosed in Monfardini et al. *Bioconjugate Chem.*, 6, 62–69 (1995).

In the case of the compound of formula I-A, the sum of n and n' are from 300 to 1500 so as to produce a conjugate having a total average molecular weight of PEG units of from 15 to 60 kDa and preferably from 35 to 45 kDa. In the preferred embodiment of formula I-A the sum of n and n' is from about 800 to 1200 with the average sum of n and n' being from 850 to 1000. Generally, the preferred ratio of n to n' in the compounds of formula I-A and II-A is from 0.5 to 1.5 with from 0.8 to 1.2 being preferred. In the case of the compound of formula I-B, n is preferably between 300 to 1500 to produce a compound having from 300 to 1500 PEG units with a total molecular weight of from 15 to 60 kDa and preferably from 35 to 45 kDa. In the preferred embodiment n is from about 850 to 1000.

Pharmaceutical Compositions

The human or murine ob proteins prepared in accordance with this invention may be prepared in pharmaceutical compositions suitable for injection with a suitable carrier or vehicle by methods known in the art. Among the preferred carriers for formulating the homogeneous OB proteins of the invention are human serum albumen, human plasma proteins, etc.

Treating Obesity and Related Conditions and Diseases

Administration of recombinant homogeneous ob protein, be it human or murine or a combination thereof, results in decreased food intake and weight loss in obese humans and animals. Therefore, administration of the ob protein replenishes this protein which is important in the regulation of body weight. The pharmaceutical compositions containing the human or murine ob proteins may be formulated at a strength effective for administration by various means to a human or animal patient experiencing abnormal fluctuations in body weight, either alone or as part of an adverse medical condition or disease, such as type II diabetes mellitus. A variety of administrative techniques by injection may be utilized, among them subcutaneous, intravenous and intraperitoneal injections. Average quantities of the ob protein may vary and in particular should be based upon the recommendations and prescription of a qualified physician or veterinarian.

EXAMPLES

The Examples provided below are not intended to limit the invention is any way.

Example 1
Obtaining the Human ob cDNA

The human ob cDNA was obtained by screening a commercially available lambda phage cDNA library ("Clontech") made from RNA derived from human adipocyte tissue. From this library, two lambda phages each containing approximately a 2.5 kilobase fragments corresponded to the human ob cDNA sequence were obtained through hybridization of lambda phage libraries. By this technique, two clones were identified (i.e., hob1 cDNA and hob2 cDNA). The human ob gene was subcloned into the commercially available plasmid vector DNA (pBluescriptSk⁻ by "Stratagene"). The resulting vectors containing these human ob gene sequences were called pBluescriptSk⁻hob1 and pBluescriptSk⁻hob2.

The human ob gene sequence in this pBluescriptSk⁻hob1 and pBluescriptSk⁻hob2 were verified by nucleotide sequencing. The amino acid sequences of the protein deduced from the nucleotide sequencing corresponded to the human ob protein of SEQ ID. NO. 4 and as published by Zhang, et al (1994). The pBluscriptSk⁻hob1 had a T-C mutation after the stop codon of the hob1 cDNA. This mutation resulted in the loss of the StuI restriction site otherwise predicted to be present in the nucleotide sequence of hob 1 as follows:

hob1

...GGG.TGC.TGA GGCC*T* TGA... (SEQ ID NO:9)

-continued

Gly Cys stop pBluescriptSk⁻hob1

...GGG.TGC.TGA GGCCC TGA...    (SEQ ID NO:10)

Gly Cys stop pBluescriptSk⁻hob2

...GGG.TGC.TGA GGCCT TGA    (SEQ ID NO:9)

Gly Cys stop

Since this mutation in pBluescriptSk⁻hob1 is located after the stop codon of the human ob cDNA sequence it does not lead to a change in the amino acid sequence of the human ob protein as published by zhang et al.

As far as the nucleotide sequence of the cDNA present in pBluescriptSk⁻hob2 is concerned, it was demonstrated by restriction enzyme analysis that this plasmid has the StuI restriction site located after the stop codon of the human ob cDNA sequence.

In addition to the fact that pBluescriptSk⁻hob1 has a mutation in the StuI restriction site following the stop codon, the pBluescriptSk⁻hob1 also has an EcoRI restriction site after the ORF in hob1 cDNA which is absent in the hob2 cDNA. (See FIG. 1.)

Example 2
Plasmid Construction for Murine Ob Protein (mob)

Murine ob cDNA of SEQ ID NO. 1 was obtained by the procedure of Zhang et al (1994) and thereafter inserted into the pCDNA3 vector. The murine ob gene thus obtained was used to construct the expression vector pLPPsOmpA-mob for expression of the murine ob protein (mob). This expression vector and its construction is detailed in FIG. 2.

The first stage of construction was to achieve the fusion of the signal-coding sequence from sOmpA gene to the mature coding region of the murine ob gene, i.e., without its natural signal-sequence. The DNA fragment of 501 bp encoding the mature murine ob protein inserted in the pCDNA3 vector was amplified from the vector by the polymerase chain reaction (PCR) using Vent DNA polymerase (New England Biolabs), a forward primer (primer 1) starting with the first nucleotide of the codon encoding valine (which is the first amino acid in the mature mob) (Zhang et al., Nature 372:425 (1994)), and a reverse primer (primer 2) corresponding to the region of the mob containing the stop codon of mob. Primer 2 also contained a sequence corresponding to a Hind III restriction site.

```
PRIMER 1:
5' GTG CCT ATC CAG AAA GTC 3'      (SEQ ID NO:11)
   Val Pro Ile Glu Lys Val          (SEQ ID NO:12)

PRIMER 2:
5' TCCCAAGCTT TCAGCATTCAGGGCTAAC 3'  (SEQ ID NO:13)
      HindIII  stop
```

The amplified 501 bp DNA fragment was purified by agarose gel electrophoresis and phosphorylated using T4 polynucleotide kinase ("Boehringer") and next digested with the restriction enzyme HindIII to create a 5' protruding end at the position of the primer 2. The obtained fragment had a blunt end corresponding to the first nucleotide of the cDNA encoding mature mob, and a 5' protruding end corresponding to a cleaved HindIII site.

Next, the sOmpA plasmid pT10sOmpArPDI obtained by the methods of De Sutter K. et al (1994) was fused to the mob gene to create a pT10sOmpAmob plasmid. To carry this out, the mob fragment was cloned by ligation using T4 ligase ("New England-Biolabs") into the pT10sOmpArPDI vector DNA which was previously digested with the restriction enzymes NaeI and HindIII by methods known in the art (Sambrook, J. et al (1989)). This pT10sOmpArPDI plasmid was derived from plasmid p714 (a gift to Dr. W. Fiers from Dr. D. Wiley, ref. Parker and Wiley, Gene 83, p 117–134, 1989) and was obtained from the Laboratory of Molecular Biology (Dr. W. Fiers, University of Gent). This plasmid contained the cDNA encoding mature rat protein disulfide isomerase (rPDI) cDNA fused to the sOmpA sequence.

This fusion of the last codon in sOmpA (alanine) to the first codon in the cDNA of mature rPDI (glycine) created a NaeI restriction site which after cleavage with NaeI released the last codon in the sOmpA sequence and the first codon in the cDNA encoding rPDI sequence as blunt ends.

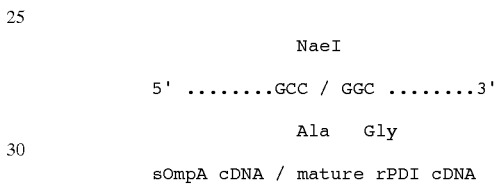

A HindIII site exists at the end of the cDNA encoding rPDI. Therefore, further digestion of this plasmid with HindIIII released the major part of the rPDI cDNA and created a 5' protruding end compatible with one of the ends of the PCR fragment. The resulting plasmid where the cDNA encoding the rPDI was replaced by the cDNA encoding mature mouse ob was called pT10sOmpAmob and is depicted in FIG. 1.

The ligated DNA was introduced in *E. coli* strain MC1061 using standard electroporation and the obtained colonies were screened for the presence of the murine ob DNA fragment by restriction enzyme analysis. Clone pT10sOmpAmob had the sequence encoding the mature murine ob protein fused to the sequence encoding sOmpA.

Next, the expression of mob in *E. coli* in this pT10sOmpAmob was placed under the control of both the lipoprotein promoter ($P_{lpp}$) and the lac promoter-operator ($PO_{lac}$). To do this, the hybrid gene sOmpA-mob sequence was transferred from the plasmid pT10sOmpAmob to the plasmid vector pLPPsOmpArPDI by standard procedures described in De Sutter et al (1994)). The pLPPsOmpArPDI plasmid was derived from plasmid p714 (a gift to Dr. W. Fiers from Dr. D. Wiley, ref. Parker and Wiley, Gene 83, p 117–134, 1989) and was obtained from the Laboratory of Molecular Biology (Dr. W. Fiers, University of Gent). For this step, the plasmid pT10sOmpAmob DNA was cleaved with the restriction enzymes XbaI and HindIII. The fragment containing the sOmpA-mob encoding DNA was then ligated into the plasmid pLPPsOmpArPDI from which the sOmpA-rPDI encoding DNA was previously removed by cleavage with the restriction enzymes XbaI and HindIII. The resulting plasmid was called pLPPsOmpAmob.

Example 3
Expression of murine ob protein in *E. coli* (MC1061)

Expression of the murine ob protein in *E. coli* was achieved as follows. The pLPPsOmpAmob plasmid constructed in accordance with Example 2 was inserted by electroporation into an *E. coli* strain MC1061. The *E. coli* cells (MC1061) harboring the plasmid pLPPsOmpAmob was grown up overnight at 28° C. in Luria-Bertania ("Difco Laboratories") medium supplemented with the antibiotic carbenicillin (100 ug/ml, "Beecham"). This culture was then used as an inoculum (100-fold dilution) for a 30 ml overnight culture at 28° C. in the same medium. This culture was then diluted 100-fold in 3 liter (e.g., 6×0.5 1 in 1 liter erlenmeyer flasks) in the above medium and shaked at 28° C. in a New Brunswick air shaker (300 rpm) for about 4 hours until a density of $A_{600}$ 0.3 to 0.5 is reached. At this time, the lac promoter was induced by addition of 2 mM final concentration of isopropyl-β-D-thiogalactopyranoside (IPTG, "Boehringer") as described in De Sutter, et al (1994). The cells were further incubated at 28° C. for about 5 hours until the cell density reached $A_{600}$ of 1.3 to 1.5. Next the cells were collected by centrifugation in a JA10 rotor (Beckman centrifuge models J2- 21 or J2-21M) for 6 min. at 6750 rpm (8000×g) at 4° C. The supernatant was removed and the cell pellet was resuspended rapidly in 250 ml icecold osmotic shock buffer (100 mM Tris-HCl, pH 7.4/ 20% sucrose/10 mM EDTA) and incubated on ice for 10 to 20 min as described by Koshland and Botstein (1980).

Thereafter, the suspension was transferred to plastic centrifuge tubes and the cells collected by centrifugation at 8200 rpm (8000×g) for 5 min. at 4° C. in a JA20 rotor. The supernatant was removed, and the cell pellet rapidly resuspended in 120 ml icecold water under vigorous shaking and incubated on ice for an additional 10 min. The suspension was then centrifuged in the JA20 rotor for 6 min. at 4° C. at 11,500 rpm (16,000×g) and the supernatant corresponding to the periplasmic fraction (osmotic shock fluid) was collected (approx. 120 ml). Sodium azide and Tris-HCl (pH 7.5) was added to a final concentration of 0.05% and 50 mM respectively. The osmotic shock fluid containing the murine ob protein was stored at −20° C. until further use.

Example 4
Expression of Murine Ob Protein in *E. coli* (MC1061)

Expression of murine ob protein was achieved in accordance with the procedure described in Example 3, except triacilline (100 μg/ml) was the antibiotic used to supplement the Luria-Bertaria medium (rather than carbenicillin).

Example 5
Purification of Murine Ob Protein from the *E. coli* Osmotic Fluid The murine ob protein located in the 120 ml. frozen osmotic shock fluid in accordance with Example 4 was purified as follows. The 120 ml osmotic shock fluid containing the murine ob protein was thawed and centrifuged at 4° C. for 20 min at 16,000 rpm in a JA20 rotor to remove insoluble debris. The supernatant was then loaded directly onto a column containing a 30 ml bedvolume Q-Sepharose Fast Flow ("Pharmacia") preequilibrated with 50 mM Tris-HCl (pH 7.5) buffer. After washing with the 50 mM Tris-HCl (pH 7.5) buffer, the mob protein was eluted with 50 mM Tris-HCl (pH 7.5) buffer containing 0.1 M NaCl.

Next, solid $(NH_4)_2SO_4$ was added to the material eluted from the Q-Sepharose Fast Flow containing column to a final concentration of 1.0 M and the mixture was loaded onto a column containing 7.5 ml bedvolume Butyl-Sepharose Fast Flow ("Pharmacia") preequilibrated with 50 mM Tris-HCl (pH 7.5) buffer containing 1.0 M $(NH_4)_2SO_4$. After washing with Tris-HCl (pH 7.5) buffer containing 1.0 M $(NH_4)_2SO_4$, the mob protein was eluted with by applying a gradient from 1.0 M $(NH_4)_2SO_4$ in 50 mM Tris-HCl (pH 7.5) buffer to 20% ethylene glycol in water. The mob protein eluted from the Butyl-Sepharose Fast Flow column at the very end of the gradient, while most contaminants eluted much earlier. The purity of the mob protein at this stage was 90% as estimated by silver-stained polyacrylamide gel electrophoresis (PAGE).

The mob protein in the material eluted from the Butyl-Sepharose Fast Flow containing column was then further purified by gel filtration chromatography. To do this, mouse ob protein was concentrated at 4° C. to a volume of 1 ml on a YM10 ("Amicon") membrane using a 8MC concentrating unit ("Amicon"), and was applied to a column (1.0 cm×50 cm) containing 39 ml GlOO-Sephadex ("Pharmacia") preequilibrated in phosphate buffered saline. The fractions containing the mob protein were then pooled and the protein concentrated on a YM10 membrane. At this stage, the mob protein was more than 95% pure as estimated by PAGE and silver staining. SDS-PAGE revealed a single protein band at Mr 15,000.

Example 6
Sequence Analysis of Murine Ob Protein

N terminal amino acid sequence of the murine ob protein obtained and purified by the procedures of Examples 2, 3, 4 and 5 described above was performed according to the procedure of Laemli, U. K. (1970). After electrotransfer of the electrophoresed proteins to a poly(4-vinyl N-methylpyridinium iodide)-coated glass fiber sheet as described by Bauw et al (1988), the band of protein with Mr 15,000 was excised from the membrane and the N-terminal amino acid sequence was determined by Edman degradation on a 470A gas-phase sequenator equipped with a 120A on-line phenylthiohydantoin amino acid analyzer ("Applied Biosystems"). The N-terminal amino acid sequence of the murine ob protein was obtained by the above described procedures was Val-Pro-Ile-Gln corresponding to the mature murine ob protein of SEQ ID NO: 3.

Example 7
Construction of Expression Vector for Human Ob Protein (hob)

Figure 3:
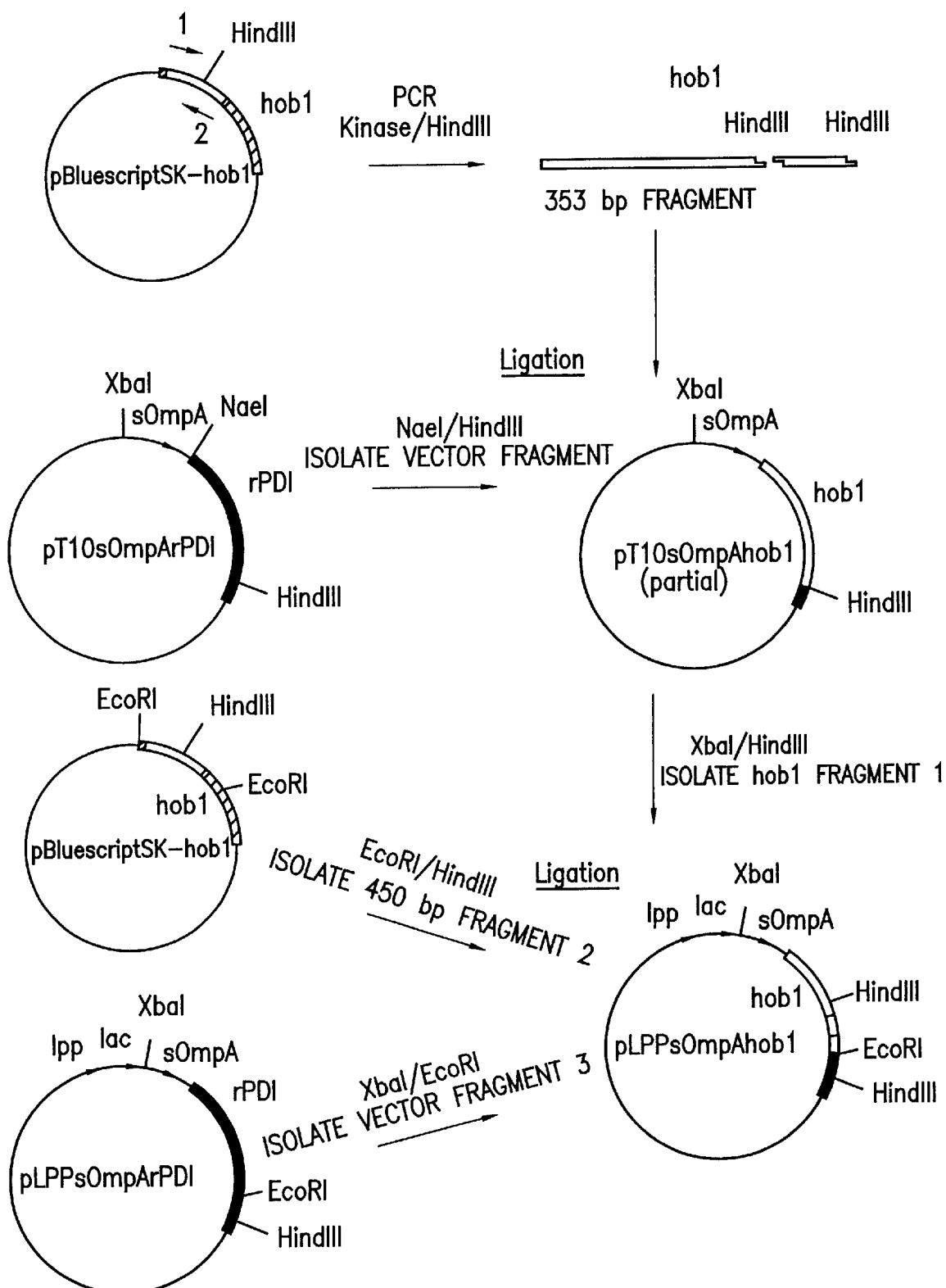
FIG. 3 is a schematic of the construction of the pLPP-sOmpA hob1 expression vector.

The human ob gene obtained in accordance with the procedures of Example 1 was utilized to construct an expression vector pLPPsOmpA-hob1 for expression of the human ob protein. This construction was similar to the construction of pLPPsOmpA-mob described in Example 2 and is detailed in FIG. 3. A three-fragment ligation was required to complete the DNA fragment containing the entire mature human ob coding sequence.

In the first stage of the construct, a hob nucleotide sequence starting with the first nucleotide of the codon encoding the first amino acid of the mature human ob protein (valine) was fused to the signal-coding sequence from OmpA (sOmpA), so that the sOmpA sequence is upstream of the 5' end of the hob nucleotide coding sequence. This DNA fragment was obtained by amplification in a PCR mixture containing plasmid pBluescriptSk⁻hob1, Vent DNA polymerase, and two primers. The forward primer (primer 1) started with the first nucleotide of the codon encoding the first amino acid of mature human ob protein, and the reverse primer (primer 2) contained the sequence of the human cDNA containing the stop codon. The amplification reaction yielded a DNA fragment of 501 bp containing the sequence encoding the mature human ob protein. The 5' end of this DNA fragment was then phosphorylated with T4 polynucleotide kinase and digested with the restricition enzyme HindIII, yielding a 353 bp DNA fragment having a blunt end corresponding to the first nucleotide of the cDNA encoding mature hob (position corresponding to the primer 1), and a 5' protruding end corresponding to a cleaved HindIIII site. This 353 bp DNA fragment was purified by agarose gel electrophoresis and cloned in the pT10sOmpArPDI plasmid which has been previously digested with the restriction enzymes Nae I and HindIII. The resulting plasmid pT10sOmpAhob1 -partial, has the DNA fragment encoding a part of the mature human ob protein (amino-terminal part) fused to the sequence encoding sOmpA.

```
Primer 1:
5' GTGCCCATCCAAAAAGTC 3'           (SEQ ID NO:14)

Primer 2:
5' TCCCAAGCTTTCAGCACCCAGGGCTGAG 3' (SEQ ID NO:15)
               stop
```

In a second step, the DNA sequence encoding the carboxy terminal part of the human ob protein (i.e., fragment 2) was ligated to the DNA fragment encoding the amino-terminal part of mature hob, and the resulting fragment encoding the entire mature hob sequence fused to the sOmpA was transferred to plasmid pLPPsOmpArPDI to bring expression of mature human ob protein in E.coli under the control of the lipoprotein promoter and the lacpromoter-operator. To do this, the plasmid pT10sOmpAhob1 -partial was digested with XbaI and HindIII and the 400 bp DNA fragment 1 of hob was isolated by agarose gel electrophoresis (fragment 1). Next the plasmid pBluescriptSk⁻hob1 was cleaved with HindIII and EcoR1, and the 450 bp was isolated by agarose gel electrophoresis (fragment 2). Finally, the plasmid pLPPsOmpArPDI was cleaved with XbaI and EcoRI, and the vector fragment isolated by agarose gel electrophoresis (fragment 3). The DNA fragments 1, 2 and 3 were then ligated to each other and the ligation mixture introduced into E. coli strain MC1061. The colony containing the final plasmid construct pLpPPsOmpAhob1 was used for expression and secretion of mature human ob protein.

Example 8
Expression of Human Ob Protein in E. coli (MC1061)

The pLPPSOmpAhob1 constructed in accordance with Example 7 was used to transform E. coli strain MC1061 for expression of the human ob protein in soluble biologically active form in the periplasm of the host E. coli cells. Insertion of the plasmid into these host E. coli cells was performed by electroporation. The E. coli cells (MC1061) harboring the plasmid pLPPsompAhob1 were grown at 28° C. in Luria-Bertania ("Difco Laboratories") medium supplemented with the antibiotic carbencillin (100 ug/ml, "Beecham") to the proper density, after which the lac promoter was induced by addition of 2 mM final concentration of isopropyl-β-D-thiogalactopyranoside (IPTG, "Boehringer") as described in De Sutter, et al (1994). The cells were further grown until the cell density reached 1.3 $A_{600}$. Next the cells were collected by centrifugation (8000×g at 4° C. ) and the cell pellet was resuspended rapidly in icecold osmotic shock buffer (100 mM Tris-HCl, pH 7.4/20% sucrose/10 mM EDTA) and incubated on ice for 10 min as described by Koshland and Botstein (1980).

Thereafter, the cells were again collected by centrifugation as above and the cell pellet was resuspended in ice cold water and incubated on ice for 10 min. The suspension was then centrifuged for 5 min. at 16,000×g and the supernatant (osmotic shock fluid) was collected. Sodium azide and Tris-HCl (pH 7.5) was added to a final concentration of 0.05% and 50 mM respectively. The osmotic shock fluid containing the human ob protein was stored at −20° C. until further use.

Example 9
Expression of Human Ob Protein in E. coli (Mc1061)

Expression of the human ob protein was achieved by using the procedure of Example 8, except triacilline (100 μg/ml) was used as the antibiotic to supplement the Luria-Bertaria medium rather than carbenicillin.

Example 10
Purification of Human Ob Protein from the E. coli osmotic Fluid

To purify the human ob protein in the osmotic shock fluid of Example 9, NaCl was added to the fluid to a final concentration of 0.1 M and the fluid was then loaded directly onto a column containing a 30 ml bedvolume Q-Sepharose Fast Flow ("Pharmacia") preequilibrated with 50 mM Tris-HCl (pH 7.5) buffer.

Next, solid $(NH_4)_2SO_4$ was added to the flow-through material eluted from the Q-Sepharose Fast Flow containing column to a final concentration of 1.0 M and the mixture was loaded onto a column containing 7.5 ml bedvolume Butyl-Sepharose Fast Flow ("Pharmacia") preequilibrated with 50 mM Tris-HCl (pH 7.5) buffer containing 1.0 M $(NH_4)_2SO_4$. After washing with Tris-HCl (pH 7.5) buffer containing 1.0 M $(NH_4)_2SO_4$, the hob protein was eluted with by applying a gradient from 1.0 M (NH4)2SO4 in 50 mM Tris-HCl (pH 7.5) buffer to 20% ethylene glycol in water. The hob protein eluted from the Butyl-Sepharose Fast Flow column at the very end of the gradient, while most contaminants elute much earlier. The purity of the hob protein at this stage was 90% as estimated by silver-stained polyacrylamide gel electrophoresis (PAGE).

The hob protein in the material eluted from the Butyl-Sepharose Fast Flow containing column was then further purified by gel filtration chromatography. To do this, human ob protein was concentrated at 4° C. to a volume of 1 ml on a YM10 ("Amicon") membrane using a 8MC concentrating unit ("Amicon"), and was applied to a column (1.0 cm×50 cm) containing 39 ml G100-Sephadex ("Pharmacia") pre-equilibrated in phosphate buffered saline. The fractions containing the hob protein were then pooled and the protein was concentrated on a YM10 membrane. At this stage, the hob protein was more than 95% pure as estimated by PAGE and silver staining. SDS PAGE analysis of the eluate revealed a single protein band at Mr 15,000.

Example 11
Purification of Human Ob Protein from the E. coli Osmotic Fluid

To purify the human protein in the osmotic shock fluid of Example 9 the procedure of Example 10 was used with the following exception: Prior to adding solid $(NH4)_2SO_4$ to the flow-through material, the following steps were carried out with regard to the osmatic shock fluid of Example 9.

The human ob protein in the osmotic shock fluid of Example 9 was loaded directly onto a column containing a 30 ml bedvolume Q-Sepharose Fast Flow ("Pharmacia") prequilibrated with 50 mM Tris-HCl (ph 7.5) buffer. After washing with the 50 mM Tris-HCl (pH 7.5) buffer, the hob protein was eluted with 50 mM Tris-HCl (pH 7.5) buffer containing 0.1 M NaCl.

Example 12
Sequence Analysis of Human Ob Protein

N terminal amino acid sequence of the human ob protein purified and obtained by the procedures of Examples 7–11 described above was performed according to the procedure of Laemli, U. K. (1970). After electrotransfer of the electrophoresed proteins to a poly(4-vinyl N-methypyridinium iodide)-coated glass fiber sheet as described by Bauw et al (1988), the band of protein with Mr 15,000 was excised from the membrane and the N-terminal amino acid sequence was then determined by Edman degradation on a 470A gas-phase sequenator equipped with a 120A on-line phenylthiohydantoin amino acid analyzer ("Applied Biosystems"). The N-terminal amino acid sequence of the hob protein obtained by the above described procedures was Val-Pro-Ile-Gln corresponding to the mature human ob protein of SEQ ID NO: 6.

Example 13
Biological Activity of Murine Ob Protein: Intracerebroventricular (ICV) Injection in ob/ob Mice The biological activity of the mature murine ob protein purified in accordance with Example 5 was determined using the ICV method as follows. Infusion cannulas were implanted into the lateral ventricle of the brains of anesthetized female obese ob/ob mice (age 6–13 weeks) using the following coordinates (2 mm lateral of midline; 0.6 mm with respect to bregma; 2 mm down) based on the methods of Haley and Mc Cormick (1957). The end of the cannula was mounted on the skull using a jeweler screw and dental cement. Mice were individually housed in plastic cages with free access to food (except for the night prior to ICV injection) and water. Following recovery from surgery as assessed by daily food intake and body weight gain, mice were studied on several occasions following the intracerebroventricular (ICV) injection of 1 ul of one of the following test solutions:

1) artificial CSF;
2) bacterial control solution;
3) ob protein (0.6 to 1 ug/mouse); or
4) no infusion.

The injection of one of the above test solutions ICV into each mice was followed by 1 ul of artificial CSF to clear the cannula. For purposes of this experiment, the bacterial control solution was an sample identically processed and prepared in accordance with the procedures outlined for Examples 2–4, except that the plasmid inserted in the E. coli bacteria was absent the murine ob gene.

Mice were fasted for 18 hours (overnight) prior to ICV injection. Mice were lightly restrained and a 10 ul Hamilton syringe fitted with a piece of precalibrated polyethylene (PE) tubing (PE20) was used to inject lul of the test solution into the cannula placed in the lateral ventricle. Mice were then immediately placed in a test cage with a food dish containing a pre-weighted amount of pelleted mouse chow and a water bottle. Mice were visually observed and food intake was measured for the next seven hours. Food intake measurements were obtained at 0.5, 1, 2, 3, 4, 6 and 7 hours post-ICV injection. Body weight for each animal was measured prior to the ICV injection and 24 hours later. Successful cannula placement was documented by an increase in 2 hour food intake following ICV injection of 10 ug Neuropeptide Y in 2 hour fasted mice according to Morley, J. E. et al (1987).

The results of the ICV test described above were as follows:

A. Reduction of Food Intake

During the first 30 minutes following ICV injection almost all mice ate with a short latency and consumed approximately 0.5 grams. Mice which received no injection or artificial CSF continued to eat throughout the next 6.5 hours and reached a cumulative 7 hour intake of 3.2 grams (Table 1). In contrast, the mice treated with ob protein ICV stopped eating after the first 30 min and did not eat again. Thus, their cumulative food intake remained suppressed over the next 6.5 hours at approximately 0.5 grams (Table 1). Mice receiving the vehicle control solution ICV also stopped eating after 30 min., and only began eating again between 6 and 7 hours.

B. Reduction in Body Weight Gain

The 24 hour change in body weight of the mice injected with vehicle control was slightly reduced from that of artificial CSF injected or non-injected mice (Table 1). However, the percent change in body weight of the mice injected with ob protein was near zero and was significantly reduced compared to the vehicle control injected mice (Table 1).

C. Conclusion

The observed effect of direct administration of recombinant mouse ob protein (1.1 ug/mouse in 1 ul to the brain) was a sustained and significant reduction in food intake and body weight gain of female ob/ob mice. This demonstrates that ob protein can act directly on the brain and is consistent with the effect of the ob protein when injected intraperitoneal. This example also confirms the biological activity of bacterially expressed recombinant murine ob protein in female obese ob/ob mice in accordance with the invention.

TABLE 1

| Treatments | Food Intake (0.7 hr) | | Body Weight Gain (0–24 hr) | |
|---|---|---|---|---|
| | g | %** | g | % |
| Artifical CSF | 3.2 ± 0.2 | 100 | 3.8 ± 0.3 | 100 |
| Vehicle Control | 0.9 ± 0.3 | 28.1 | 2.9 ± 0.2 | 76 |
| Ob Protein (1 μg/mouse) | 0.5 ± 0.1* | 15.6 | 0.3 ± 0.5* | 8 |

*indicates significant differences between ob protein and artificial CSF groups with $p < 0.05$.
**indicates percent of control Example 14
Biological Activity of Murine Ob Protein Intravenous (IV) in Ob/Ob Mice The biological activity of the murine ob protein obtained and purified in accordance with Examples 2, 3, 4 and 5 was tested by intravenous (IV) injection in obese ob/ob mice as follow.

Male and female obese ob/ob mice (6–13 weeks old) were implanted with chronic jugular cannulas under pentobarbital anesthesia (80 mg/kg body weight) according to the method of Mokhtarian A., et al. (1993). Mice were individually housed in plastic cages under constant environment conditions with a 12 hr dark/12 hr light cycle. Body weights were measured in fusion daily and the patency of cannulas was verified and maintained every other day by infusion of <0.1 ml sterile heeparin/saline solution (50 U/ml in 0.9% saline). After complete recovery from surgery, assessed by body weight gain, the mice were fasted 16–18 hours (overnight). The next morning, mice were weighed and placed in test cages for 45 minutes for acclimatization before the experiment. Water was available contintously. Mouse ob protein (3 ug in 0.1 ml) or an equal volume of vehicle control or saline (0.9%) solution was injected intravenously. Awake mice were lightly restrained and 0.5 ml insulin syringes were used to inject 0.1 ml of the test solution followed by 0.05 ml heparin/saline. Trials were separated by at least 3 days. Mice were then immediately replaced in the test cage with a pre-weighted petri dish containing a pellet of mouse chow. Mice were visually observed and food intake was measured for the next seven hours at 0.5, 1, 2, 3, 4, 6 and 7 hrs post-IV injection. Body weight was measured before the IV injection and again 24 hrs later. Two separate groups of cannulated mice (11 ob/ob and 12 lean) were used in five individual trials. Most mice received mouse ob protein and one or both control injections in counterbalanced order. Two separate preparations of mouse ob protein were used in this experiment. The data reported here are a combination of the results of these individual replications.

A. Results

The results of the above experiment are as follows:

During the first 30 minutes following IV injection most obese and lean mice ate with a short latency and consumed approximately 0.3–0.5 grams. Food intake in saline and vehicle control injected obese mice increased throughout the experiment. The cumulative food intake of obese ob/ob mice injected with vehicle control was not different from the food intake of similarly fasted obese mice that were injected with saline. In contrast, the food intake of the obese ob/ob mice injected with recombinant ob protein was significantly reduced and remained suppressed at 57% of control (Table 2). No other behavioral effects were observed in the vehicle control and ob protein groups throughout the 7 hr observation period. As expected, the 24 hr post-injection body weight gain was not different in the treatment groups (Table 2) due to the limited duration of action of a single IV bolus of mouse ob protein.

B. Conclusions

These results demonstrate that recombinant mouse ob protein significantly reduced cumulative 7 hr food intake following IV administration (3 μg/mouse) in obese ob/ob mice. The ability of recombinant mouse ob protein to reduce food intake in obese ob/ob mice is consistent with the food intake results obtained following repeated IP injection of the ob protein in obese ob/ob mice. This example also confirms the biological activity of bacterially expressed recombinant mouse ob protein in female obese ob/ob mice.

TABLE 2

IV Administration of Murine Ob Protein in Ob/Ob Mice

| Treatments | Food Intake (0–7 hr) | | Body Weight Gain (0–24 hr) | |
|---|---|---|---|---|
| | g | %** | g | % |
| Saline (n = 4) | 1.8 ± 0.2 | | 2.9 ± 0.3 | |
| Vehicle Control (n = 7) | 1.4 ± 0.3 | 100 | 2.2 ± 0.6 | 100 |
| Ob Protein (1 μg/mouse) (n = 8) | 0.8 ± 0.2* | 57 | 1.4 ± 0.6 | 64 |

Data are mean ± sem.
n = indicates the number of individual mice.
*indicates significant differences between ob protein and artificial CSF groups with $p < 0.05$.
**indicates percent of control Example 15
Biological Activity of the Murine Ob Protein: Repeated IP Injection in Ob/Ob Mice.

The biological activity of the murine ob protein obtained and purified in accordance with Examples 2–5 was tested by repeated intraperitoneal (IP) injection in obese ob/ob mice as follows.

Three groups of six female obese ob/ob mice were studied. Mice were housed in plastic cages (three per cage) under constant environmental conditions with a 12 hour dark/12 hour light cycle. Twenty-four (24) hour food intake and body weight were measured every day. Following an adaptation period to environmental conditions and daily handling and injections, the mice were sorted into three treatment groups. Each mouse received two intraperitoneal (IP) injections each treatment day (shortly before the beginning of the dark phase of the dark/light cycle and three hours into the dark phase) of the 0.1 ml of the following test solutions:

1) saline (0.9%);
2) bacterial control solution; or
3) murine ob protein (3 μg/0.1 ml).

The bacterial control solution was a sample identically processed and prepared in accordance with the procedures outlined for Examples 2–4 to obtain and purify murine ob protein, except that the plasmid inserted in the E. coli bacteria was absent the murine ob gene. Mice were treated twice daily for five days and then received no treatment for two days. Food intake of each cage was measured at 2, 3, 5 and 24 hours following the first IP injection on each treatment day.

The results of the above experiment are as follows:

A. Reduction of Food Intake

Food intake was not different in the saline and bacterial control injected mice on treatment and non-treatment days throughout the one week experiment (Table 3). However, food intake was reduced in the six mice injected with 6 ug ob protein on treatment days throughout the experiment. The reduction in food intake was observed at 2, 3, 5 and 24 hours after the first injection on treatment days in the mice receiving ob protein group compared to the bacterial control and saline control groups.

B. Reduction of Body Weight Gain The cumulative body weight gain over the five treatment days of the ob protein group was −3.3±0.7 grams compared to −0.9±0.2 grams in the saline and −0.7±0.4 grams in the bacterial control groups (Table 3).

C. Conclusion

This example demonstrates that two daily IP injections of bacterially expressed recombinant murine ob protein (6 ug/mouse/day) resulted in a significant, sustained reduction of food intake and a significant decrease in the rate of weight gain of treated female ob/ob mice compared to saline and bacterial control treated ob/ob mice. These results demonstrate the bacterial expressed murine ob protein is biologically active and has the expected anti-obesity effects on genetically obese ob/ob mice in accordance with this invention. In Table 3 the 2 and 5 hour results are the mean daily food intake while the 24 hour results shown are the 5 day cumulative food intake.

PBS containing 0.1% (w/v) mouse serum albumin (albumin control) as the vehicle control solution.

A. Reduction of Food Intake

During the first 30 minutes following ICV injection almost all mice ate with short latency and consumed approximately 0.5 grams. Mice which received no injection continued to eat throughout the next 6.5 hours and reached a comulative 7 hour intake of 1.8 grams (Table 4). Mice receiving the albumin control solution ICV also stopped eating after 30 minutes and only began eating again between 3 and 7 hours. In contrast, the mice treated with human ob protein ICV ate significantly less in the first 30 minutes (0.2 grams) and ate very small amounts during the next 6.5 hours. Thus, their cumulative food intake remained suppressed over the next 6.5 hours at approximately 0.4 grams (Table 4).

B. Reduction in Body Weight Gain

The 24 hour change in body weight of the mice injected with vehicle control was slightly reduced from that of artificial CSF injected or non-injected mice (Table 4). However, the percent change in body weight of the mice injected with human ob protein was near zero (Table 4).

C. Conclusion

The observed effect of direct administration of recombinant human ob protein (0.05 $\mu$g/mouse in 1 $\mu$l) to the brain to lead to a substained and significant reduction in food intake and body weight gain of female ob/ob mice demonstrates that ob protein can act directly on the brain and is consistent with the effect of ob protein when injected IP. This example also confirms the biological activity of bacterially expressed recombinant human ob protein in female obese ob/ob mice.

TABLE 3

Repeated IP Administration of Murine Ob Protein in Ob/Ob Mice

| | Food Intake (grams/3 mice) | | | | | | Body Weight Gain grams |
|---|---|---|---|---|---|---|---|
| | 2 hr | | 5 hr | | 24 hr | | |
| Treatment | g | % of control | g | % of control | g | % of control | |
| No Injection | 5.5 ± 0.5 | | 14.5 ± 0.5 | | 44.3 ± 3.5 | | −0.9 ± 0.2 |
| Control | 7.0 ± 0.5 | 100 | 16.5 ± 1.5 | 100 | 49.5 ± 6.1 | 100 | −0.7 ± 0.4 |
| Ob Protein | 3.5 ± 0.5* | 50 | 5.5 ± 1.0* | 33 | 25.5 ± 4.6* | 52 | −3.3 ± 0.7* |

Data are mean ± sem for six ob/ob mice in each group.
Food intake is mean cumulative intake for cages of three mice during the five days of treatment at 2, 5 and 24 hr after the first IP injection.
Body weight gain is the cumulative change in body weight during the five days of treatment.
*indicates significant differences between ob protein and vehicle groups with $p < 0.05$.

Example 16
Biological Activity of Human Ob Protein: Intracerebro Ventricatar (ICV) Injection in Ob/Ob Mice The methods used to determine biological activity of Human Ob protein by intracerebroventricular ICV injection in Ob/Ob Mice were the same as Example 13 except that the test solutions were:

Recombinant human ob protein produced in Example 11 (0.05 $\mu$g) in phosphate buffered saline (PBS) containing 0.1% mouse serum albumin; and

TABLE 4

ICV Administration of Human Ob Protein in Ob/Ob Mice

| | Food Intake (0–7 hr) | | Body Weight Gain (0–24 hr) | |
|---|---|---|---|---|
| Treatments | g | %** | g | %** |
| No Injection (n = 3) | 1.8 ± 0.2 | | 3.1 ± 0.4 | |

TABLE 4-continued

ICV Administration of Human Ob Protein in Ob/Ob Mice

| Treatments | Food Intake (0–7 hr) | | Body Weight Gain (0–24 hr) | |
|---|---|---|---|---|
| | g | %** | g | %** |
| Albumin Control (n = 3) | 1.0 ± 0.4 | 100 | 1.7 ± 0.6 | 100 |
| Human Ob Protein (1 μg/mouse) (n = 5) | 0.4 ± 0.2* | 40 | 0 ± 0.8 | 0 |

Data are mean ± sem.
n = indicates the number of individual mice.
*indicates significant differences between human ob protein and artificial CSF groups with $p < 0.05$.
**indicates percent of control Example 17
Biological Activity of Ob Protein in Obese Human Subjects: Reduction of Test Meal Intake Following IV Administration The biological activity of the murine and human ob proteins obtained and purified in accordance with Examples 7–11 respectively, is determined by measuring test meal intake following IV administration to humans as follows.

Lean and obese human volunteers are presented with test meals of fixed caloric content in an eating laboratory on two occasions using the method of Muurahainen, N. E. et al (1991). At least one hour prior to meal presentation, an indwelling IV catheter is placed in the antecubital or forearm vein and is kept open with a heparin lock. Visual-analog hunger rating are obtained 15 minutes before, 15 minutes after meal presentation, and at the conclusion of the test meal. Murine or human ob protein or saline is then infused IV 20 minutes prior to meal presentation. Each subject is instructed to eat as much of the test meal as they wish until they are satisfied. The amount of the test meal ingested by each subject is measured. Each subject then receives infusions of either human ob protein (0.5 mg/kg body weight), murine ob protein (0.5 mg/kg body weight) or saline and the difference in amount of the test meal ingested under these conditions is calculated. In the human or murine ob protein group, there is a reduced amount of meal consumed by at least 20%.

Example 18
Biological Activity of Ob Protein in Obese Human Subjects: Induction of Weight Loss by Repeated IV Administration The biological activity of the murine and human ob proteins obtained and purified in accordance with Examples 7–11, respectively, is determined by measuring weight loss following repeated IV administration of the ob protein, according to the following method.

A placebo controlled, double blind weight loss study using the methods of Drent, M. L. et al (1995) is performed. Obese subjects (BMI greater than 27) are weighed and then placed on a diet with 1500 Kcal for a 2–4 week run-in period at the end of the run-in period, all obese subjects that lost at least 1 kg body weight are randomized into two treatment groups matched for weight loss during the run-in phase. Subjects receive daily IV administration of either human or murine ob protein (0.5 mg/kg/day) or placebo (saline) for at least 6 weeks. body weigh is recorded weekly. Those subjects receiving human or murine ob protein have a significant reduction in body weight than the placebo group after 6 weeks of treatment.

Example 19
A. Preparation of Polyethylene Glycol Conjugated OB Protein From E. coli Cells 50 g. of E. coli cell pellet prepared in Example 8 prior to resuspension was suspended with 1L of 50 mM Tris-HCl (pH 8.5) containing 50 mM EDTA. The suspension was incubated for 15 minutes at 37° C., diluted with an additional 1L of 50 mM Tris-HCl (pH 8.5) containing 5 mM EDTA. Thereafter, the suspension was homogenized using a homogenizer for 15 minutes at 50% power setting. The suspension was clarified by centrifugation at 8,000 rpm, 4° C. for one hour. The pellet was discarded. The supernatant was diluted with water to a conductivity of 1.8 mS, and applied directly onto a column packed with 200 ml of Q-Sepharose Fast Flow (strong anionic ion exchange resin), preequilibration with 50 mM Tris-HCl (pH 8.5). After washing with the equilibration buffer, the adsorbed OB protein was eluted fran the column with the same equilibration buffer which additionally contained 100 mM NaCl. The eluate obtained after treating the column with the equilibration buffer contained sodium chloride was called Q-Sepharose Eluate.

Solid NaCl was added to the Q-Sepharose Eluate to reach the final conductivity to 82 mS. After this, the eluate was applied onto a Hydrophobic Interaction Column (HIC) packed with 200 ml butyl-Sepharose Fast Flow, preequilibrated with 50 mM Tris-HCl (pH 8.5) containing 1M NaCl. The unadsorbed materials were washed away with equilibration buffer and the adsorbed OB protein was eluted with 50 mM ammonium acetate (pH 6.9) to produce HIC eluate. The OB protein in the HIC eluate was determined to be 95% pure by reverse phase HPLC. The purified OB protein was concentrated to 3.7 mg/ml using a sizing membrane (YM-10). The sizing membrane was a membrane which retained molecules of 10,000 daltons or greater. After this concentration step, by using a sizing membrane, the OB protein was diafiltered into 100 mM borate buffer (pH 8.0) which was used as the OB stock solution.

B. Pegylation of Human OB Protein

In carrying out this pegylation reaction, the $PEG_2$-NHS reagent of formula II-A wherein R is $CH_3$, the sum of n and n' range from 820 to 1040 with the average sum being about 930 and having an average molecular weight of 40 kDa which was purchased from Shearwater Polymers, Huntsville, Alabama was utilized. This was a mixture of $PEG_2$-NHS reagents of formula II-A where the ratio of n to n' is approximately 1.0 and the sum of n and n' in this mixture ranged from 820 to 1040 units with the average molecular weight of the PEG chain in this mixture being approximately 20 kDA so that the average molecular weight of the reagent is approximately 40 kDA with the average sum of n and n' in this mixture being about 930. To 2 mg or 0.54 ml of the 3.7 mg/ml purified human OB stock solution prepared above in part A [125 nmoles OB protein], there was added 250 n moles of the aforementioned $PEG_2$-NHS reagent solution. This solution consisted of 10 mg or 0.1 ml of the 100 mg/ml $PEG_2$-NHS reagent solution in 1 mM HCl. The total reaction mixture was made up to 0.67 ml by adding 100M borate pH5.0. Final molar ratio of protein to reagent was 1:2. This mixture was stirred at 4° C. for 4 hours and the reaction was stopped by the addition of 1 microliter of glacial acetic acid to produce a final pH of 4.5. The resulting reacting mixture (0.67 mL) was diluted with water to form a 27 ml. solution which was loaded onto a column containing 1.7 ml of carboxy methylated cationic exchange resin [Popos Perseptives, Framingham, Massachusetts]. The column was equilibrated with 3.3 μM HEPES/MES/Sodium acetate buffer pH 5.0. The diluted reaction mixture was applied to the column and unadsorbed $PEG_2$-NHS reagent was washed off the column. The adsorbed pegylated and unmodified OB proteins were eluted with step salt gradients [15 column volumes each] of 80, 150 and 500 mM NaCl. 2ml of these eluates were separately collected in sequence and the samples of each fraction were subjected to an SDS-PAGE analysis. From this analysis, the eluants were classified as highly pegylated conjugates, desired branched mono-PEG-OB ($PEG_2$-OB) and unmodified OB protein. Each of these fractions were pooled into the classifications set forth above and the second pool containing the desired branched mono-$PEG_2$-OB protein. This desired protein had the structure of compound of formula I-A wherein the sum of n and n' was approximately 820–1040, with the average sum being about 930, R and R' are CH3 and the average molecular weight of each PEG chain was about 20 kilodaltons. The pegylated product had an average molecular weight of about 56 kDA. The pool containing the $PEG_2$-OB was concentrated to 3.7 mg/ml using a YM 10 membrane. YM 10 is a sizing membrane which retains molecules having molecular weight of 10,000 daltons or greater. After the sizing step, concentrated material was diafiltered into a PBS buffer (pH 7.3) and stored frozen at −20° C. This stored product was the pegylated OB protein of Formula I-A where the sum of n and n' was approximately 820 to 1040 and the average molecular weight of each OB chain was approximately 20kDA. The average molecular weight of the PEG protein in this OB protein conjugate mixture was 56 kDA.

Example 20
Biological Assay of Pegylated Human OB Protein: Single IP Injection in Ob/Ob Mice
Methods Two groups of six mice female obese ob/ob mice were studied. Mice were housed in plastic cages (three/cage) under constant environmental conditions with a 12 hr dark/12 hr light cycle. 24 hr food intake and body weight were measured every day. Following an adaptation period to environmental conditions, daily handling and injections, the mice were sorted into two treatment groups. Each mouse received one intraperitoneal (IP) injections on day 1 of the experiment (just before the beginning of the dark phase of the dark/light cycle) of the 0.1 ml of the following solutions: Saline (0.9%); human OB protein stock solution prepared in part A of Example 19 (30 μg/0.1 ml); pegylated control solution (an identically processed and purified sample without human OB protein) or pegylated OB protein (30 μg/0.1 ml) prepared as described in Example 19. Mice were injected only once, on day 1. Daily food intake of the cage and the body weight of each mouse was measured for the next three days and again on day 6.
Results A) Reduction of Food Intake Daily food intake was not different in the saline and pegylation control injected mice on the single treatment and two subsequent days (Table 5). However, daily intake was reduced in the six mice injected with 30 μg human ob protein and pegylated human OB protein on the treatment day (5.2, 8.2 vs 11.9, 11.4 g) compared to the saline and pegylated control injected mice. The food intake of the mice injected with human OB protein returned to control levels, while the food intake of the mice injected with pegylated human OB protein remained reduced on the subsequent days of the experiment. The reduction in food intake was observed 48 hrs after the single injection in the pegylated human OB protein group. The cumulative 24 hr food intake over the three days of the experiment was significantly reduced to 49% of control in the pegylated human OB protein compared to the saline and pegylation control group.

B) Reduction of Body Weight Gain

Change in body weight was not different in the saline and pegylation control injected mice on the single treatment and two subsequent days (Table 6). However, body weight was reduced in six mice injected with 30 μg human Ob protein and pegylated human OB protein on the treatment day (−0.9, −0.7 vs 0.1, 0.3 g) coared to the saline and pegylated control injected mice. The body weight of the mice injected with human OB protein returned to control levels, while the body weight of the mice injected with pegylated human OB protein continued to decrease on the subsequent days of the experiment. The continued reduction in body weight was observed 48 hrs after the single injection in the pegylated human OB protein group. The cumulative change in body weight over the six days of the experiment was −1.6 grams compared to 0.4 grams in the OB protein group, 0.7 grams in the saline and 1.1 +0.2 grams pegylation control groups (Table6).

Conclusion

This example demonstrates that a single IP injection of pegylated human OB protein (30 μg/mouse) resulted in a significant, sustained reduction of food intake and a significant decrease in body weight of treated female ob/ob mice over three days compared to saline and pegylation control treated ob/ob mice. These results demonstrate the pegylated human OB protein has sustained, potent biologically active and has the expected antiobesity effects on genetically obese ob/ob mice.

TABLE 5

Daily Food Intake of a Single IP Administration of Pegylated Human OB Protein in Ob/Ob Mice

| | Food Intake (/3 mice/day) | | | | | |
|---|---|---|---|---|---|---|
| | day 1 | | day 2 | | day 3 | |
| Treatment | g | o% f control | g | % of control | g | % of control |
| Saline | 11.9 | 100 | 13.7 | 100 | 13.6 | 100 |
| OB Protein | 5.2 | 43.7 | 11.7 | 85.4 | 12.5 | 92 |
| Pegylated Control | 11.4 | 95.8 | 4.5 | 106 | 13.4 | 99 |
| Pegylated OB | 8.2 | 68.9 | 6.0 | 43.8 | 4.9 | 36 |

TABLE 5-continued

Daily Food Intake of a Single IP Administration
of Pegylated Human OB Protein in Ob/Ob Mice

| | Food Intake (/3 mice/day) | | | | |
|---|---|---|---|---|---|
| | day 1 | | day 2 | | day 3 |
| Treatment | o% f g | % of control | g | % of control | g % of control |
| Protein | | | | | |

Data are mean for six ob/ob mice in each group. Food intake is mean daily food intake for cages of three mice on each day of the experiment after the single IP injection on day 1. Note persistent reduction in daily food intake only in the pegylated OB protein group.

TABLE 6

Change in Body Weight of a single IP Administration
of Pegylated Human OB Protein in Ob/Ob Mice

| Treatment | Change in Body Weight (grams) | | | |
|---|---|---|---|---|
| | day 1 | day 2 | day 3 | day 6 |
| Saline | 0.1 | 0.6 | 0.01 | −0.01 |
| OB Protein | −0.9 | 1.1 | 0.2 | ND |
| Pegylated Control | 0.3 | 0.4 | 0.6 | −0.2 |
| Pegylated OB Protein | −0.7 | −0.6 | −0.9 | 0.6 |

Data are mean for six ob/ob mice in each group. Mice received a single IP injection on Day 1 only. Change in body weight is the change in body weight on each of the days of the experiment. Note persistent weight loss only in the pegylated OB protein group. ND in the Table indicates not determined.

REFERENCES

1. Zhang, Y. et al. Positional cloning of the mouse obese gene and its human homologue. *Nature* 372: 425–432 (1994).
2. Grundy, S. M. & Barnett, J. P. *Disease-a-Month* 36: 645–696 (1990).
3. Ingalls, A. M. et al. *J. Hered.* 41: 317–318 (1950).
4. Friedman J. M. et al *Genomics* 11: 1054–62 (1991).
5. Haley, T. J. and Mc Cormick, W. G. Pharmacological effects produced by intracerebral injection of drugs in conscious mouse. *Brit. J. Pharmacol.* 12: 12–15 (1957)
6. Sambrook, Fritsch and Maniatis, *Molecular Cloning: A Laboratory Manual*, Second Edition (1989) Cold Spring Harbor Laboratory Press, Cold Spring Harbor, New York).
7. *DNA Cloning: A Practical Approach,* Vol. I and II (D. N. Glover, ed. 1985), MRL Press, Ltd., Oxford, U.K.).
8. Benton and Davis, *Science* 196: 180 (1977).
9. Grunstein and Hogness, *Proc. Nat. Acad. Science* 72: 3961 (1975).
10. Pouwels, et al, *Cloning Vectors: A Laboratory Manual,* (Elsevier, N. J., 1985).
11. Parker and Wiley, *Gene* 83: 117 (1989)
12. De Sutter, K. et al. *Gene* 141: 163–170 (1994).
13. Studier et al, *J. Mol. Biol.* 189: 113 (1986).
14. Lauer, *J. Mol. Appl. Genet.* 1: 139–147 (1981).
15. Maniatis, *Molecular Cloning: A Laboratory Manual* (Cold Spring Harbor Laboratory, 1982, p 412).
16. Goeddel et al. *Nucleic Acids Research* 8, 4057 (1980).
17. Siebenlist et al., *Cell* 20, 269 (1980).
18. Casadaban, M. J. and Cohen, S. N. Analysis of the gene control signals by DNA fusion and cloning in *Escherichia coli. J. Mol. Biol.* 138: 179–207 (1980)),
19. Koshland, D. and Botstein, D.: Secretion of beta-lactamase requires the carboxy end of the protein. *Cell* 20: 749–760 (1980).
20. Laemli, U. K Cleavage of structural proteins during the assembly of the head of bacteriophage T4. *Nature* 227: 680–685 (1970).
21. Matsudaira. P., *J. Biol Chem.* 262: 10035 (1987).
22. Muurahainen, N. E., et al. Effect of a soup preload on reduction of food intake by cholecystokinin in humans. *Am. J. Physiol* 260: R672-R680 (1991).
23. Drent, M. L., et al. Orlistat (RO 18-0647), a lipase inhibitor, in the treatment of human obesity: a multiple dose study. *Int. J. Obesity* 19: 221–226 (1995).
24. Bauw, G., et al. Orotein-electroblotting on polybase-coated glass-fiber and polyvinylidene difluoride membranes: an evaluation. *J. Biol. Chem.* 7: 194–196 (1988).
25. Morley, J. E., et al. Neuropeptide Y increases food intake in mice. *American J. Physiol.* 253: R516–R522 (1987).
26. Mokhtarian, A, et al Chronic vasacular catherization in the mouse. Physiol. Behav. 54: 895 (1993).

What is claimed is:

1. A composition comprising one or more conjugates of polyethylene glycol linked to a polypeptide, said polypeptide being a homogeneous purified biologically active human OB protein comprising SEQ ID NO: 6 or a homogeneous purified biologically active murine OB protein comprising SEQ ID NO: 3, characterized in that said polypeptide 1) when administered ICV to 16–18 hour fasted mature obese ob/ob mice having a body weight of at least 30 grams at a dose of 20 µg or less,
     a) reduces food intake during a 5 hour feeding test by 50% compared to vehicle injected control mice (ED50 for reducing food intake); and
     b) reduces body weight gain during the 24 hours following the ICV injection by at least 50% compared to vehicle injected control mice (ED50 for reducing body weight gain);

2) when administered IP to non-fasted mature ob/ob mice having a body weight of at least 30 grams twice a day at the beginning of daylight and again at the 3 hour point of the dark phase, for one week, in a total daily dose of 10 µg or less,
     a) reduces 5 and 24 hour food intake by at least 20% compared to vehicle injected control mice (ED20 for reducing food intake); and
     b) reduces body weight gain during the 24 hours following the first IP injection by at least 20% compared to vehicle injected control mice (ED20 for reducing body weight gain)

with the average molecular weight of the polyethylene glycol units in said conjugates within said composition being between 15 kDa to 60 kDa.

2. The composition of claim 1 wherein said protein is the human OB protein.

* * * * *